US007943301B2

(12) United States Patent
Sen et al.

(10) Patent No.: US 7,943,301 B2
(45) Date of Patent: May 17, 2011

(54) DNA CONFORMATIONAL SWITCHES AS SENSITIVE ELECTRONIC SENSORS OF ANALYTES

(75) Inventors: Dipankar Sen, Burnaby (CA); Richard P. Fahlman, Surrey (CA)

(73) Assignee: Simon Fraser University, Burnaby, British Columbia (CA)

( * ) Notice: Subject to any disclaimer, the term of this patent is extended or adjusted under 35 U.S.C. 154(b) by 898 days.

(21) Appl. No.: 10/507,387

(22) PCT Filed: Mar. 11, 2003

(86) PCT No.: PCT/CA03/00330

§ 371 (c)(1),
(2), (4) Date: May 9, 2005

(87) PCT Pub. No.: WO03/076653

PCT Pub. Date: Sep. 18, 2003

(65) Prior Publication Data

US 2005/0205434 A1    Sep. 22, 2005

Related U.S. Application Data

(60) Provisional application No. 60/362,928, filed on Mar. 11, 2002.

(51) Int. Cl.
*C12Q 1/68* (2006.01)
*A61K 49/00* (2006.01)
*C12P 19/34* (2006.01)
*C07H 21/02* (2006.01)
*G01N 33/566* (2006.01)

(52) U.S. Cl. ............ 435/6; 424/9.1; 435/91.1; 436/501; 536/23.1; 536/24.2

(58) Field of Classification Search ............. 435/6, 91.1, 435/91.31, 455; 536/23.1, 24.2, 24.5; 436/501; 424/9.1

See application file for complete search history.

(56) References Cited

U.S. PATENT DOCUMENTS

| | | | |
|---|---|---|---|
| 6,144,869 A * | 11/2000 | Berner et al. ............... | 600/347 |
| 6,221,586 B1 | 4/2001 | Barton et al. | |
| 6,238,870 B1 * | 5/2001 | Meade et al. ................ | 435/6 |
| 2003/0087239 A1 * | 5/2003 | Stanton et al. ............... | 435/6 |

OTHER PUBLICATIONS

Breaker,R., Current Opinion in Biotech., vol. 13, pp. 31-39 (2002).*
Gasper et al, J. Am. Chem. Soc., vol. 119, pp. 12,762-12,771 (1997).*
Giese, Bernd—Long-Distance Charge Transport in DNA The Hopping Mechanism—Acc. Chem. Res. 2000, 33, 631-636—Department of Chemistry, University of Basel, St. Johanns-Ring 19, CH-4056 Basel, Switzerland.
Schuster, Gary B.—Long-Range Charge Transfer in DNA: Transient Structural Distortions Control the Distance Dependence—Acc. Chem. Res. 2000, 33, 253-260—School of Chemistry and Biochemistry, Georgia Institute of Technology, Atlanta, Georgia 30332.
Kelley, Shana O.; Holmlin, R. Erik; Stemp, Eric D.A.; and Barton, Jacqueline K.—J. Am. Chem. Soc. 1997, 119, 9861-9870—Bechman Institute, Division of Chemistry and Chemical Engineering, California Institute of Technology, Pasadena, CA 91125.
Giese, Bernd and Wessely, Stefan—The Influence of Mismatches on Long-Distance Charge Transport Through DNA—Angew. Chem. Int. Ed. 2000, 39 No. 19—Wiley-VCH Verlag GmbH, D-69451 Weinheim, 2000.
Boon, Elizabeth M.; Ceres, Donato M.; Drummond, Thomas G.; Hill, Michael G.; and Barton, Jacqueline K.—Mutation Detection by Electrocatalysis at DNA-Modified Electrodes—Division of Chemistry and Chemical Engineering, CA Inst. of Tech., Pasadena, CA 91125.
Rajska, Scott R.; and Barton, Jacqueline K.—How Different DNA-Binding Proteins Affect Long-Range Oxidative Damage to DNA—Biochemistry 2001, 40, 5556-5564—Division of Chemistry and Chemical Engineering, California Institute of Technology, Pasadena, CA 91125.
Gasper, Susan M. and Schuster, Gary B.—Intramolecular Photoinduced Electron Transfer to Anthaquinones Linked to Duplex DNA: The Effect of Gaps and Traps on Long Range Radical Cation Migration—J. Am. Chem. Soc. 1997, 119, 12762-12771—School of Chemistry and Biochemistry, Georgia Institute of Technology, Atlanta, Georgia 30332.
Fink, Hans-Werner and Schoenberger, Christian—Electrical Conduction Through DNA Molecules—*Letters to Nature*, 1999 Macmillan Magazines Ltd.—Institute of Physics, University of Basel, Klingelbergstrasse 82, CH-4056 Basel, Switzerland—vol. 398, Apr. 1, 1999.
Okahata, Yoshio, et al.—Anistropic Electric Conductivity in an Aligned DNA Cast Film—*Communications to the Editor*—J. Am. Chem. Soc. 1998, 120, 6165-6166—1998 American Chemical Society—Dept. of Biomolecular Engineering, Tokyo Inst. of Tech.
Hall, Daniel B., et al.—Oxidative DNA Damage Thorough Long-Range Electron Transfer—*Letters to Nature*—Nature, vol. 382, Aug. 22, 1996—Division of Chemistry and Chemical Engineering, CA Inst. of Technology, Pasadena, CA 91125.
Kino, K. and Saito, I., "Product Analysis of GG-Specific Photooxidation of DNA via Electron Transfer: 2-Aminoimidazolone as a Major Guanine Oxidation Product", J. Am. Chem. Soc., 1998, 120, 7373-7374.

(Continued)

*Primary Examiner* — Jane Zara
(74) *Attorney, Agent, or Firm* — Chernoff Vilhauer LLP

(57) ABSTRACT

The electrical conductivity of DNA and other oligonucleotide constructs is dependent on its conformational state. Such a dependence may be harnessed for the electronic sensing of external analytes, for instance, adenosine. Such a DNA sensor incorporates an analyte receptor, whose altered conformation in the presence of bound analyte switches the conformation, and hence, the conductive path between two oligonucleotide stems, such as double-helical DNA. Two distinct designs for such sensors are described that permit significant electrical conduction through a first or "detector" double-helical stem only in the presence of the bound analyte. In the first design, current flows through the analyte receptor itself whereas, in the second, current flows in a path adjacent to the receptor. The former design may be especially suitable for certain categories of analytes, including heterocycle-containing compounds such as adenosine, whereas the latter design should be generally applicable to the detection of any molecular analyte, large or small. Since analyte detection in these DNA sensors is electronic, the potential exists for their application in rapid and automated chip-based detection of small molecules as well as of proteins and other macromolecules.

42 Claims, 15 Drawing Sheets

OTHER PUBLICATIONS

Sanii, L. and Schuster, G.B., "Long-Distance Charge Transport in DNA: Sequence-Dependent Radical Cation Injection Efficiency", J. Am. Chem. Soc. 2000, 122, 11545-11546.

Odom, D.T. et al., "Charge transport through DNA four-way junctions", Nucleic Acids Research 2001, 29(10), 2026-2033.

Fahlman, R.P. and Sen, D., "DNA Conformational Switches as Sensitive Electronic Sensors of Analytes", J. Am. Chem. Soc. Apr. 2002, 124(17), 4610-4616.

Fan, C. et al., "Electrochemical interrogation of conformational changes as a reagentless method for the sequence-specific detection of DNA", PNAS 2003, 100(16), 9134-9137.

Hall, Daniel B. and Barton, Jacqueline K., Sensitivity of DNA-Mediated Electron Transfer to the Intervening-Stack: A Probe for the Integrity of the DNA Base Stack, J. Am. Chem. Soc., vol. 119, No. 21, 1997, 5045-5046.

Kan, Yongzhi and Schuster, Gary B., Long Range Guanine Damage in Single-Stranded DNA: Charge Transport through a Duplex Bridge and in a Single-Stranded Overhang, J. Am. Chem. Soc., vol. 121, No. 47, 1999, 10857-10864.

Porath, Danny et al., Direct measurement of electrical transport through DNA molecules, Nature, vol. 403, Feb. 10, 2000, 635-637.

Rajski, Scott R. et al., Protein-Modulated DNA Electron Transfer, J. Am. Chem. Soc., vol. 121, No. 23, 1999, 5615-5616.

Battiste, John L. et al., Binding of an HIV Rev Peptide to Rev Responsive Element RNA Induces Formation of Purine-Purine Base Pairs, Biochemistry, vol. 33, No. 10, 1994, 2741-2747.

Lin, Chin H. and Patel, Dinshaw J., Structural basis of DNA folding and recognition in an AMP-DNA aptamer complex: distinct architectures but common recognition motifs for DNA and RNA aptamers complexed to AMP, Chemistry and Biology 1997, vol. 4 No. 11, 817-832.

Szalai, Veronika A. and Thorp, H. Holden, Electron Transfer in Tetrads: Adjacent Guanines Are Not Hole Traps in G Quartets, J. Am. Chem. Soc., vol. 122, No. 18, 2000, 4524-4525.

Soukup, Garrett A. and Breaker, Ronald R., Allosteric Nucleic Acid Catalysts, Current Opinion in Structural Biology 2000, 10:318-325.

Kelley, Shana O. et al., Long-Range Electron Transfer through DNA Films, Angew. Chem. Int. Ed., 1999, 38, No. 7, 941-945.

Bixon, M., et al.—Long-Rang Charge Hopping in DNA—PNAS, Oct. 12, 1999, vol. 96, No. 21, pp. 11713-11716—School of Chemistry, Tel Aviv Univ., Ramat Aviv, Tel Aviv 69978, Israel.

Saito, Isao, et al.—Photoinduced DNA Cleavage Via Electron Transfer: Demonstration That Guanine Residues Located 5' to Guanine are the Most Electron-Donating Sites—J. Am. Chem. Soc. 1995, 117, 6406-6407.

Gold, Larry, et al.—Diversity of Oligonucleotide Functions—Annu. Rev. Biochem. 1995. 64:763-97.

Hermann, Thomas and Patel, Dinshaw J.—Adaptive Recognition by Nucleic Acid Aptamers—*Science's Compass Review*—Feb. 4, 2000, vol. 287, Science.

Aich, Palok, et al.—M-DNA: A Complex Between Divalent Metal Ions and DNA Which Behaves as a Molecular Wire—J. Mol. Biol. (1999) 294, 477-485—Article No. jmbi. 1999.3234.

Peattie, Debra A.—Direct Chemical Method for Sequencing RNA—Proc. Natl. Acad. Sci. USA, vol. 76, No. 4, pp. 1760-1764, Apr. 1979 Biochemistry—Department of Biochemistry and Molecular Biology, Harvard University, Cambridge, Massachusetts 02138.

Puglisi, Joseph D. et al.—Conformation of the TAR RNA-Arginine Complex by NMR Scpectroscopy—Science vol. 257, Jul. 3, 1992.

Odom, Duncan T. and Barton, Jacqueline K.—Long-Range Oxidative Damage in DNA/RNA Duplexes—*Biochemistry 2001*, 40, 8727-8737—American Chem. Soc.

Lilley, David M. J.—All Change at Holliday Junction—Proc. Natl. Acad. Sci. USA, vol. 94, pp. 9513-9515, Sep. 1997.

Huizenga, David E., et al.—A DNA Aptamer That Binds Adenosine and ATP—Biochemistry 1995, 34, 656-665—1995 American Chemical Society.

Odom, Duncan T. et al.—Robert Charge Transport in DNA Double Crossover Assemblies—Research Paper—*Chemistry & Biology 2000*, 7:475-481—Division of Chemistry and Chemical Engineering, California Institute of Technology, Pasadena, CA 91125.

Telser, Joshua—*DNA Duplexes Covalently Labeled at Two Sites: Synthesis and Characterization by Steady-State and Time-Resolved Optical Spectroscopies*—J. Am. Chem. Soc. 1989, 111, 7226-7232—1989 American Chemical Society.

Author Unknown—*Amine-Reactive Probes*—Molecular Probes—Product Information—Revised: Dec. 8, 2003.

Hall, Daniel B., et al.,—Oxidative DNA Damage Through Long-Range Electron Transfer—*Letters to Nature*—Nature, vol. 382, Aug. 22, 1996—Division of Chemistry and Chemical Engineering, California Institute of Technology, Pasadena, CA 91125.

Nunez, Megan E; Hall, Daniel B.; and Barton, Jacqueline K.—Long-Range Oxidative Damage to DNA: Effects of Distance and Sequence—Research Paper, *Chemistry & Biology*, Feb. 1999, 6:85-97.

Henderson, Paul T., et al.—*Long-Distance Charge Transport in Duplex DNA: The Phonon-Assisted Polaron-Like Hopping Mechanism*—Proc. Natl. Acad. Sci. USA, vol. 96, pp. 8353-8358, Jul. 1999—School of Chemistry and Biochemistry, Georgia Institute of Technology, Atlanta, GA 30332.

Grinstaff, Mark W.—*How Do Charges Travel Through DNA?—An Update on a Current Debate*—Highlights, Angew. Chem. Int. Ed. 1999, 38, No. 24—Wiley-VCH Verlag GmbH, D-69451 Weinheim, 1999.

Saito, Isao—*Mapping of the Hot Spots for DNA Damage by One-Electron Oxidation: Efficacy of GG Doublets and GGG Triplets as a Trap in Long-Range Hole Migration*—J. Am. Chem. Soc. 1998, 120, 12686-12687—1998 American Chemical Society.

Wellinger, R. J. and Sen, D.—*The DNA Structures at the Ends of Eukaryotic Chromosomes*—European Journal of Cancer, vol. 33, No. 5, pp. 735-749, 1997.

Simonsson, Tomas—*G-Quadruplex DNA Structures—Variations on a Theme*—Biol. Chem., vol. 382, pp. 621-628, Apr. 2001, Medical Research Council, Laboratory of Molecular Biology, Hills Road, Cambridge CB2 2QH, UK.

Giese, Bernd, et al.—Direct Observation of Hole Transfer Through DNA By Hopping Between Adenine Bases And By Tunnelling—*Letters to Nature*, Nature, vol. 412, Jul. 19, 2001 Macmillan Magazines Ltd.

Nakatani, Kaxuhiko, et al.—*N2-Phenyldeoxyguanosine: Modulation of the Chemical Properties of Deoxyguanosine toward One-Electron Oxidation in DNA*—J. Am. Chem. Soc. 2002, 124, 6802-6803—Department of Synthetic Chemistry and Biological Chemistry, Faculty of Engineering, Kyoto University.

Saito, Isao, et al.—Photoinduced DNA Cleavage via Electron Transfer: Demonstration That Guanine Residues Located 5' to Guanine Are the Most Electron-Donating Sites—*J. Am. Chem. Soc.* 1995, 117, 6406-6407—1995 American Chemical Society.

Wang, Yong, et al.—RNA Molecules That Specifically and Stoichiometrically Bind Aminoglycoside Antibiotics with High Affinities—*Biochemistry 1996*, 35, 12338-12346, 1996 American Chemical Society—Dept. of Biological Chemistry and Molecular Pharmacology, Harvard Medical School, 250 Longwood Avenue, Boston, Massachusetts 02115.

Mao, Chengde, et al.—A Nanomechanical Device Based on the B-Z Transition of DNA—*Letters to Nature*, Nature, vol. 397, Jan. 14, 1999—1999 Macmillan Magazines Ltd.

\* cited by examiner

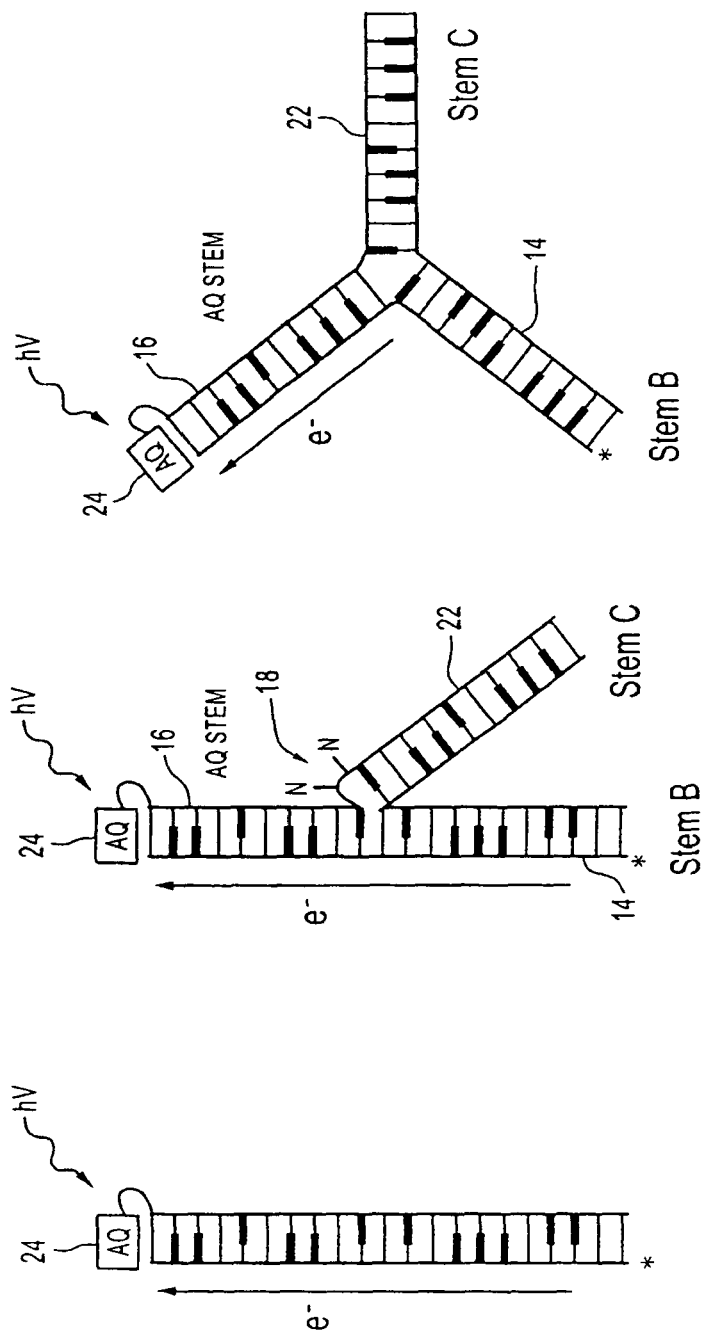

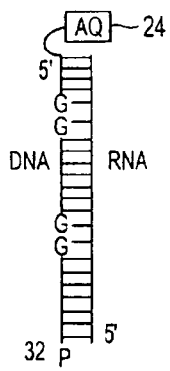
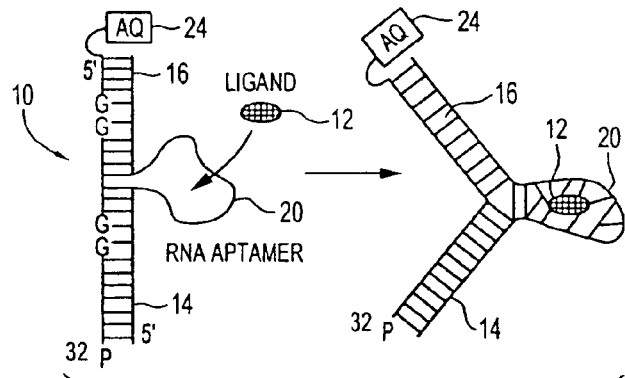
FIG. 3(a)  FIG. 3(b)
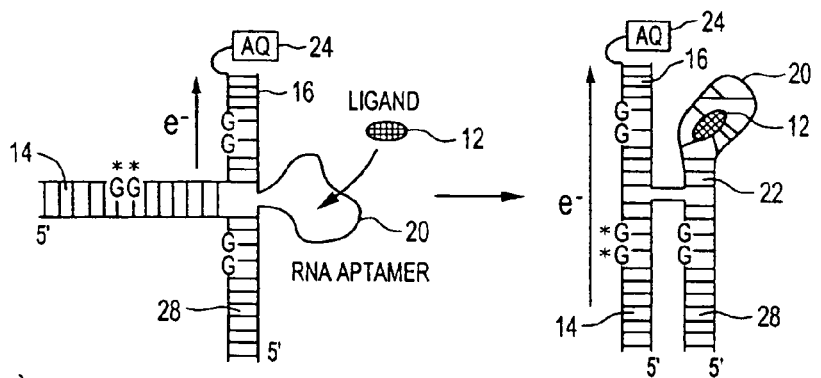
FIG. 3(c)
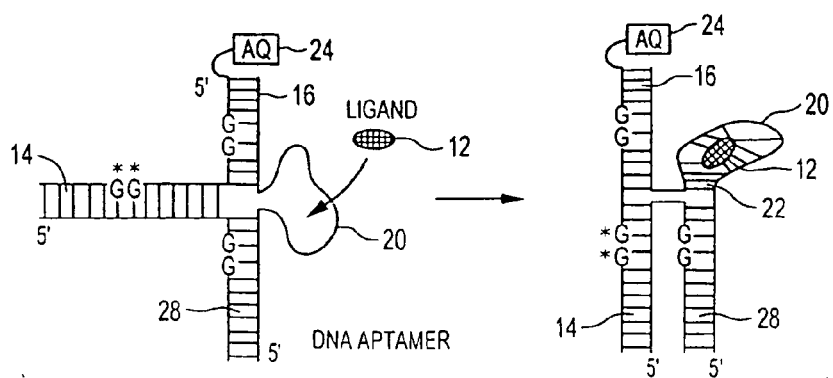
FIG. 3(d)
In (c) and (d), asterisks indicate guanines through which electron conduction may be expected to change subject to ligand binding to the ligand receptor/aptamer.

A sensor for detecting specific DNA or RNA oligonucleotides

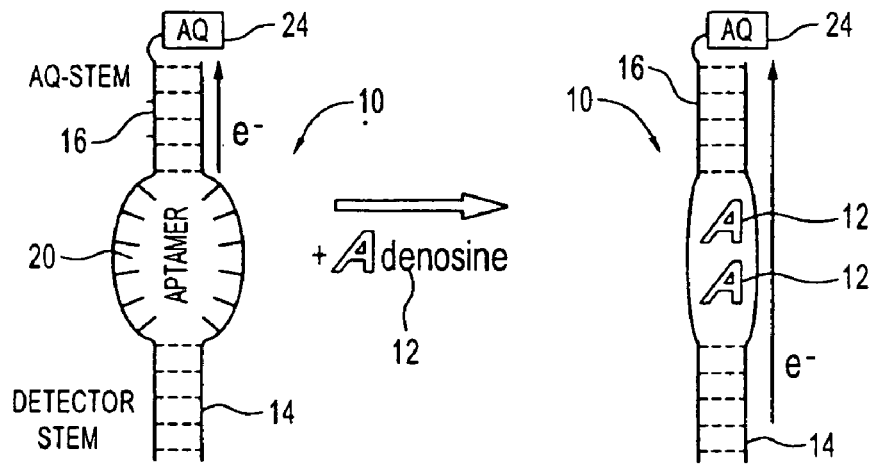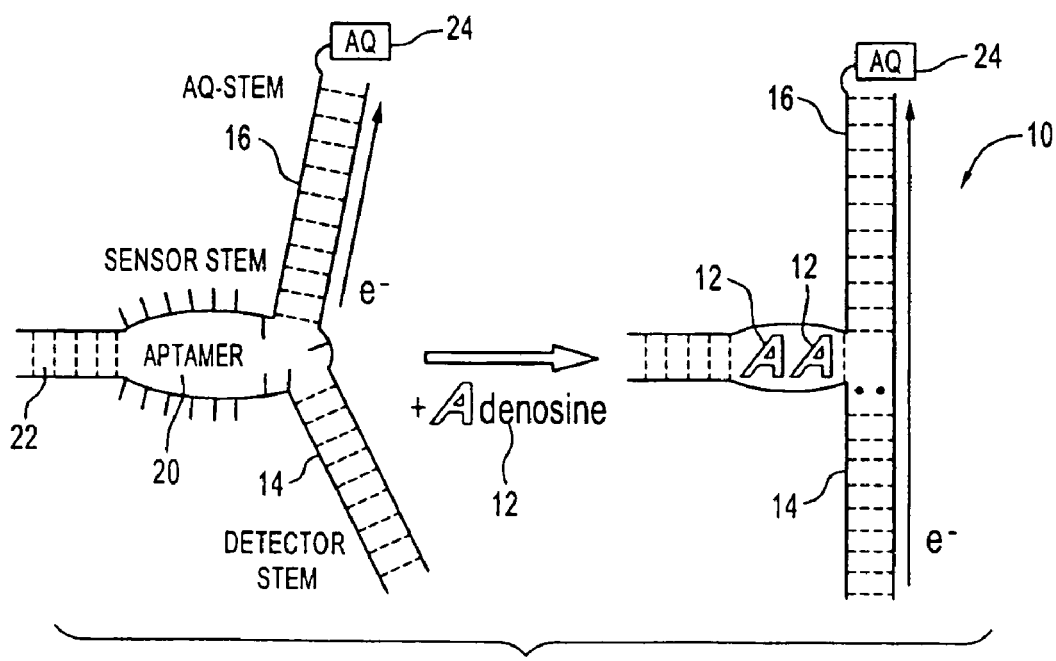
FIG. 11

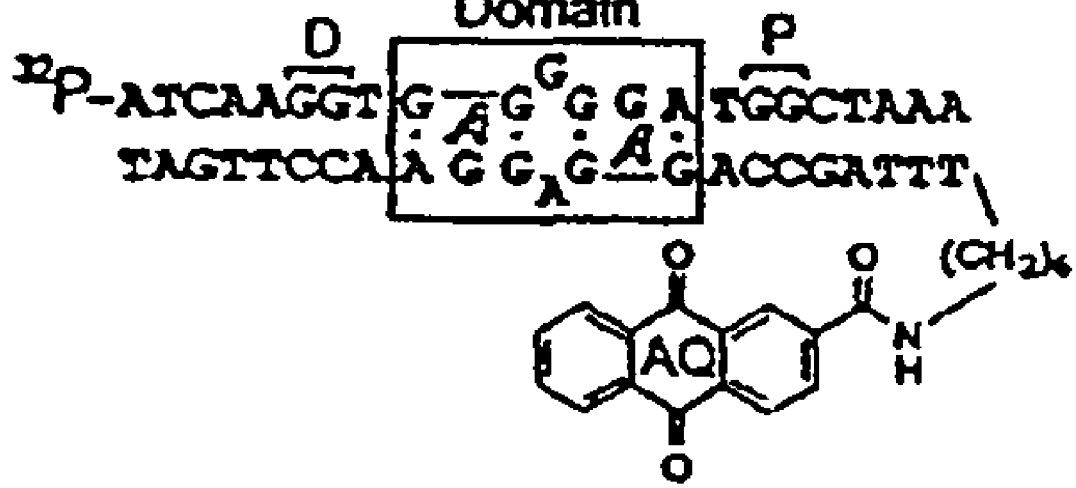
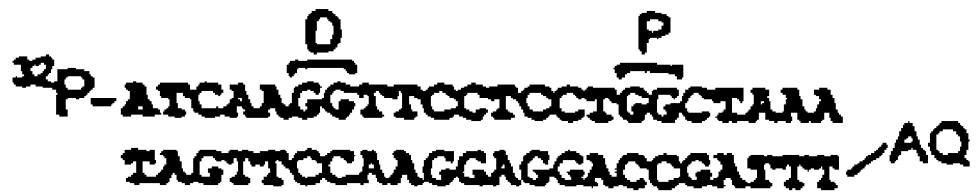
FIG. 12

DNA CONFORMATIONAL SWITCHES AS SENSITIVE ELECTRONIC SENSORS OF ANALYTES

REFERENCE TO RELATED APPLICATION

This application claims the benefit of the filing date of U.S. provisional patent application No. 60/362,928 filed 11 Mar. 2002.

TECHNICAL FIELD

This application relates to biosensors comprising DNA or other oligonucleotides for electronically detecting the presence of analytes. The sensors rely on changes in DNA conformation induced by binding of a target analyte to a receptor site of the sensor. The conformational changes modulate changes in charge transfer through the DNA, which is detectable either directly or indirectly.

BACKGROUND

Despite a lack of complete understanding of the mechanistic details of electron transfer through DNA, long-range electron transfer in double-stranded DNA is generally believed to be the result of a multi-step-bopping reaction[1-2]. The consensus view is that a continuous base-stacking throughout the DNA duplex is essential for efficient charge transfer. It has been shown that efficiency of charge transfer is reduced in duplexes containing mismatches[3-5] and bulges[6]. Proteins that bind and disrupt continuous base-stacking in duplex DNA also reduce the efficiency of electron transfer past the site of helix disruption[7-8]. Despite the importance of a continuous base stack, not all perturbations to the helix prevent charge transfer, as it has been observed in helices containing abasic sites[9] and through short, single stranded overhangs[10]. However, even these latter structures are believed to base-stack to some extent, which permits charge transfer through them.

Detection of charge transfer in DNA has been detected both directly and indirectly. Dehydrated DNA duplexes[11] or DNA fibers[12a,b] positioned between metal electrode have had their conductivity measured directly. Indirect measurement of DNA conductivity has been made in aqueous solution, after inducement of charge transfer with a photoexcitable moiety (such as anthraquinone[13], or rhodium(III) complexes with aromatic ligands[14]). The photoexcitable moiety is attached to one end of a duplex such that it lies in intimate contact with the π-stack of the DNA base pairs. The photoexcited states of anthraquinone and rhodium(III) complexes are powerful oxidising agents, and are able to collect electrons from guanines (via generation of a mobile radical cation, or electon hole) within the DNA duplex, from reported distances of up to >200 Å away from the ligand[15a,b]). According to the putative "multi-step hopping" mechanism referred to above, the radical cation moves from guanine to guanine (guanine is the base with the lowest ionization potential). A guanine upon which the mobile radical cation is transiently localized is somewhat susceptible to reaction with water and dissolved oxygen, leading to, the formation of oxidation products such as diaminooxazalone and 2-aminoimidazalone[16]. As described herein, the position of the latter products along a DNA strand can readily be detected by sequencing gel-electrophoresis, since these products are base-labile and cause site-specific strand breakage on being treated with hot piperidine.

Despite disagreements on the precise mode of charge transfer within DNA duplexes, investigators are in agreement that the electrical conductivity of DNA is dependent on its conformational state—specifically, on the integrity of its π-stacking. While much of the research on DNA conduction has focused on "static" or relatively immobile DNA structures, the purpose of the present invention is to exploit changes in the conductivity of DNA, dependent on changes in its conformational state, to provide information about the DNA's environment—such as the presence or absence of a specific analyte. In other words, if conformational change in the DNA results from the binding of a particular analyte, then this should correlate with a change in the DNA's conductivity, providing the basis for an analyte sensing device constructed from DNA or other oligonucleotides.

In nature, DNA is known to bind a variety of small molecules as well as macromolecular ligands. However, recent innovations in in vitro selection (SELEX) methods have resulted in DNA (as well as RNA) "aptamer" sequences, which are capable of specifically binding a variety of molecular species, including many that normally do not interact with DNA or RNA[17]. Such aptamer oligonucleotides frequently exhibit induced-fit folding behaviour (reviewed by Hermann & Patel[18]), whereby the aptamer itself, largely unstructured in solution, undergoes significant compaction and structural stabilization upon binding its cognate ligand.

Barton and colleagues[19] have reported the electronic detection of a DNA-binding protein, HhaI methyltransferase, by virtue of the protein's interference in the charge conduction path of a duplex DNA. HhaI methylase works by binding to a target G*CGC site on a double-helix, and extruding the target cytosine base (marked with an asterisk, above) out of the helix in order to methylate it. This extrusion naturally disrupts the conduction path through the helix and, thus, the level of conduction through the helix. While this approach demonstrates protein-modulation of charge-transfer through DNA, it requires the selection of a protein capable of extruding a base out from the DNA helix and is therefore not of general application. For example, unlike the present invention, the method could not be readily extended as a means for the detection of any protein, large or small, DNA-binding or not.

It is also known in the prior art to detect conformational change in duplex DNA by binding of divalent metal ions. Lee and colleagues[20] have reported a methodology for the electronic detection of a DNA-binding protein. Following the binding of the protein to its binding site upon a DNA duplex, the DNA is converted to a metal-bound form ("M-DNA"), with a significantly higher conductivity than that of standard B-DNA. The presence of the bound protein, however, interferes with M-DNA formation by its binding site, and therefore affects the overall conductivity of the duplex. While this approach is promising, the efficacy of this method for use in the detection of proteins that do not naturally bind to DNA, or which bind to non-duplex elements of DNA or RNA, has not yet been reported.

The need has therefore arisen for improved biosensors of general application for analyte detection. Since the detection means is electronic, the potential exists for use of such sensors for rapid and automated chip-based detection of small molecules as well as of proteins, macromolecules and other analytes. The sensors are also potentially useful as nanoelectronic switches and junction devices simulating solid state electronic logic gates.

SUMMARY OF INVENTION

In accordance with the invention, an analyte sensor comprising a first oligonucleotide stem, a second oligonuleotide stem, and a receptor site capable of binding the analyte is provided. The receptor site is operatively connected to the first and second stems. The sensor is alterable between a first conformational state substantially impeding charge transfer between the first and second stems and a second conformational state permitting charge transfer between the first and second stems. The sensor switches between the first conformational state and the second conformational state when the analyte binds to the receptor site.

The charge may be conducted between the first and second stems through the receptor site in the second conformational state. Alternatively, the receptor site may be removed from the conduction path between the first and second stems such that the receptor does not function as a conductor in either of the first and second conformational states.

In one embodiment of the invention the sensor switches from the first conformational state to the second conformational state (i.e. resulting in increased charge transfer) when the analyte binds to the receptor site. In another embodiment, the sensor switches from the second conformational state to the first conformational state (i.e. resulting in decreased charge transfer) when the analyte binds to the receptor site. In either case, the change in charge transfer is measurable to detect the presence of the analyte. The receptor site may be configured to bind to an analyte which does not ordinarily bind to DNA The receptor site may comprise a nucleic acid apatmer selected for binding affinity to a target analyte. The first and second oligonucleotide stems may each comprise helical DNA. In the first conformational state the base stacking of the helical DNA may be discontinuous or spacially distorted or misaligned in a switch region located at or near the receptor site in the first conformational state. When the analyte binds to the receptor, a conformational change, to the second conformation state occurs, resulting in removal or lessening of the base stacking distortion or misalignment. This in turn results in increased charge transfer between the first and second stems in this embodiment.

In one embodiment of the invention a detector may be electrically coupled to the first stem and may directly measure the change in charge transfer through the sensor resulting from analyte binding. The detector may, for example, comprise a conductor or semi-conductor chip.

In other embodiments of the invention the change in charge transfer resulting from binding of the analyte to the sensor may be detected indirectly. For example, a charge flow inducer may be coupled to one of the first and second stems for triggering charge flow in at least one of the first and second stems. The charge flow inducer may comprise, for example, a photoexcitable moiety, such as antraquinone or rhodium (III), coupled to the second stem. In these examples the photoexcited states of such compounds are oxidizing agents which cause a net flow of electrons toward the photoexcitable moiety. If the sensor is in the second conformational state this process results in the formation of oxidization products which may be detected, for example, by gel-electrophoresis. For example, the gel-electrophoresis may identify damage to specific guanine residues concomitant with electron donation (and hence indicative of increased charge transfer between the first and second stems).

In one embodiment of the invention the sensor may comprise a third oligonucleotide stem which includes the receptor site. The first, second and third stems may be connected together at a three-way junction. The binding of the analyte to the receptor site on the third stem modulates charge transfer between the first and second stems. At least one of the stems may include unpaired nucleotides in the first conformational state (e.g. non-Watson-Crick base pairs located near the three-way junction). Further, the sensor could optionally include a fourth oligonucleotide stem connected to the first, second and third stems at a four-way junction. The stems could each comprise helical DNA. Sensors constructed from other multi-stem nucleotide sensors (e.g. five, six or more nucleotide stems) may be configured in the same manner. In each case a conformational change to at least some of the stems occurs upon binding of the target analyte, which is detectable by directly or indirectly identifying a change in charge conduction.

In a further alternative embodiment of the invention pairs of sensors may be configured to simulate digital electronics logic gates. Each sensor is notionally operable in one of two operating states, namely "conducting" (i.e. "on") and "non-conducting" (i.e. "off"). For example, the sensor may comprise two separate receptor sites and may only switch between the first and second conformational states when both of the receptors bind to their respective target analytes.

A method for detecting the presence of an analyte is also disclosed. The method includes the steps of (a) providing a sensor comprising first and second oligonucleotide stems and a receptor site operatively connected to the first and second stems and capable of binding the analyte as described above; (b) inducing a charge flow in one of the first and second stems of the detector; and (c) detecting any change in charge transfer between the first and second stems upon binding of the analyte to the receptor.

The step of detecting changes in electrical charge transfer may include electrically coupling a conductor or semiconductor detector to the first stem and measuring the change in charge transfer resulting from analyte binding. Alternatively, a charge flow inducer coupled to the sensor could be triggered to produce an oxidizing agent. According to this protocol, the sensor is then tested for oxidation products. For example, the sensor could be heated in the presence of piperidine. The formation of oxidation products, and the specific site of DNA cleavage, may then be detected by gel electrophoresis. The direct or indirect detection of changes in electrical charge transfer may also be accomplished by other means known in the art, such as flourescence quenching.

BRIEF DESCRIPTION OF DRAWINGS

In drawings which describe embodiments of the invention, but which should not be construed as restricting the spirit or scope of the invention in any way.

FIG. 2(a) is a schematic view illustrating electrical conduction through a conventional DNA double helix having an anthraquinone moiety covalently tethered thereto.

FIG. 2(b) illustrates a sensor incorporating two unpaired nucleotides located at a 3-way junction in accordance with one embodiment of the invention.

FIG. 2(c) is a schematic view of a DNA construct having a standard 3-way junction.

FIG. 3(a) is a schematic view of a RNA/DNA heteroduplex.

FIG. 3(b) is a schematic view of a mixed or composite sensor comprising separate RNA and DNA strands.

FIGS. 3(c) and 3(d) are schematic views of sensors having 4-way junctions.

FIG. 11 is a schematic view showing the design of "integrated-ligand" and "coupled-ligand" sensors for detecting the analyte adenosine. In the absence of analyte, both sensors adopt open, unstructured conformations, which only allow charge transfer (indicated by arrows) in the oligonucleotide stem conjugated to the anthraquinone (AQ) moiety. Adenosine binding induces the folding and compaction of the adenosine aptamer, facilitating charge transfer from the detector to the AQ stems.

FIG. 12 compares the nucleotide sequence of a control duplex (SEQ ID NO:1 and SEQ ID NO:2) with the aptamer domain of the analyte sensor of FIG. 11 (SEQ ID NO: 3 and SEQ ID NO: 4) (showing two bound adenosines). The extent of the aptamer domain is indicated (shown as boxed), with the two bound adenosines shown as outlined 'A's. "D" and "P" indicate guanine doublets distally and proximally located, respectively, relative to the covalently conjugated anthraquinone (AQ) moiety.

DESCRIPTION

1.0 Description of Alternative Embodiments

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive, sense.

As used in this patent specification, the following terms shall have the following respective meanings:

"analyte" means a molecular entity capable of binding to a receptor. Analyte may include chemical compounds, such as hormones or drugs, antigens, metabolic cofactors, nucleotides, nucleic acid segments, ligands, peptides, proteins, carbohydrates, fats or any other organic or inorganic materials capable of binding to a receptor.

"aptamer" means a single or multi-stranded non-naturally occurring nucleotide sequence that functions as a receptor. Aptamers may be identified by in vitro selection methods such as SELEX.

"oligonucleotide stem" means singly or multi-stranded RNA, DNA or nucleic-acid like molecules capable of base pairing and permitting charge conduction under suitable conditions. The term includes stems composed of non-naturally occurring nucleic acid analogues, modified nucleic acids, non-standard nucleic acids and composite DNA/RNA constructs.

"receptor" means a site on a sensor capable of binding an analyte. A receptor may comprise nucleic acids, proteins, other organic or inorganic materials, or combinations thereof. The term receptor includes naturally occurring receptor sites, aptamers, and rationally designed artificial receptor sites created de novo other than by SELEX selection.

This application relates to sensors 10 for electrically sensing the presence (and optionally the concentration) of analytes 12. As described below, sensors 10 may be configured to bind to a wide range of target analytes 12, such as antigens associated with particular disease states.

Figure 1A:
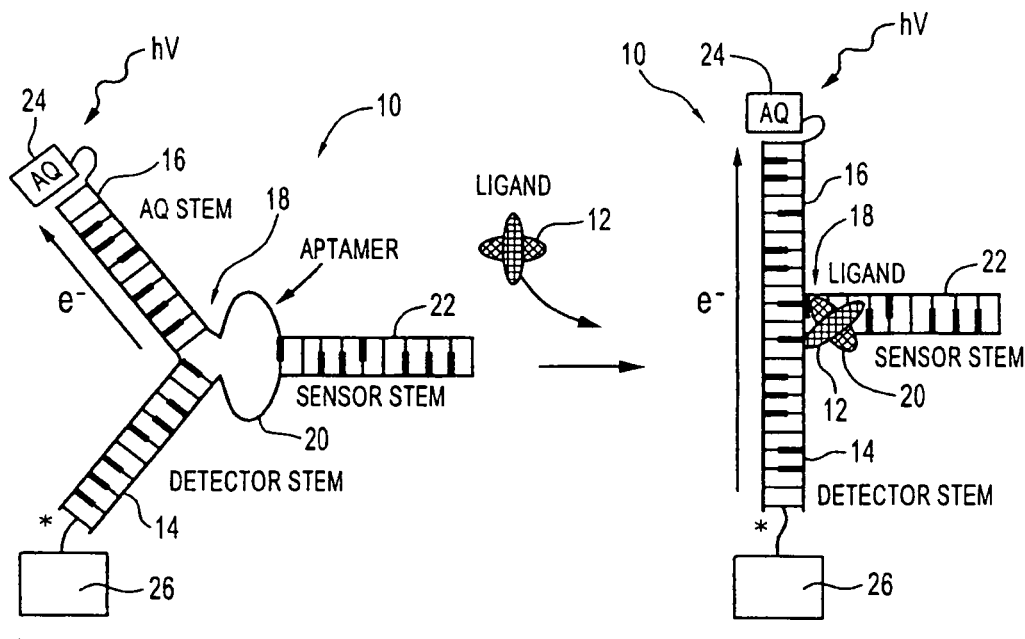
FIG. 1(a) is a schematic view of the Applicant's sensor design in the "coupled receptor" or "coupled ligand" embodiment. The sensor is altered froth a first conformational state (left) to a second conformational state (right) upon binding of an analyte (e.g. a ligand) to permit charge transfer in the direction indicated by arrows.

As shown generally in FIG. 1(a), sensor 10 includes a first oligonucleotide stem 14 and a second oligonucleotide stem 16 which are connected together at a junction 18. Stems 14, 16 may consist of double helical DNA, for example. In other embodiments oligonucleotide stems 14, 16 may comprise other nucleic acid constructs, including constructs containing synthetic or modified nucleic acid residues capable of base pairing.

Sensor 10 also includes a receptor 20 which forms part of junction 18 or is located proximate thereto. Receptor 20 may consist of any organic or inorganic site capable of binding to an analyte. By way of example, receptor 20 may consist of a nucleic acid aptamer sequence selected to bind to a target analyte.

Figure 1B:
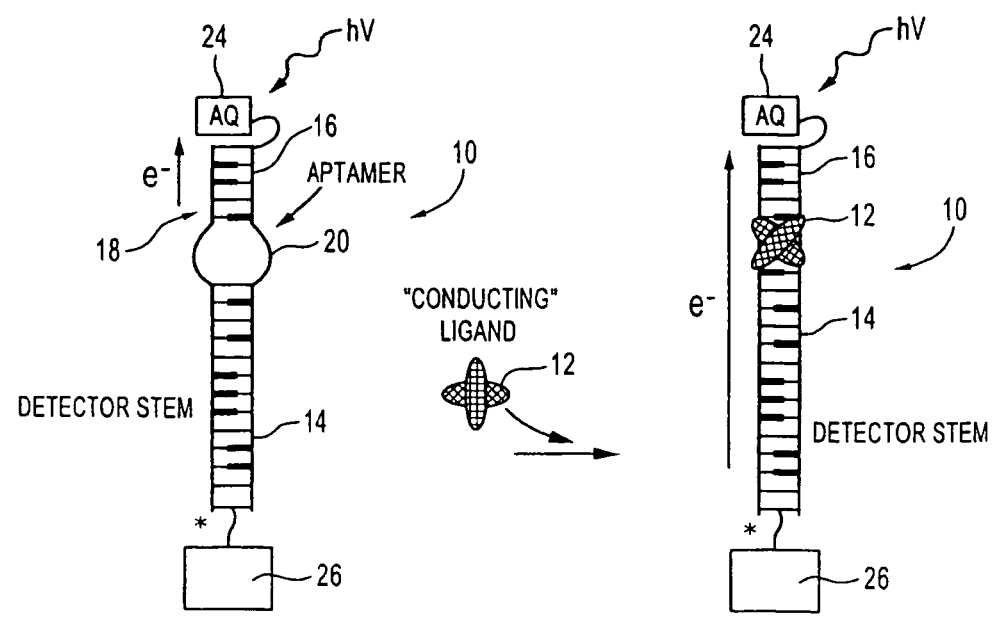
FIG. 1(b) is a schematic view of the Applicant's sensor design in the "integrated receptor" or "integrated ligand" embodiment. As in FIG. 1(a), the sensor is altered from a first conformational state (left) to a second conformational state (right) upon binding of an analyte (e.g. a ligand).

In the illustrated embodiment first stem 14 functions as an electron donor and second stem 16 functions as an electron sink (although the reverse configuration would function similarly so long as a net charge transfer in either direction is established). As described in detail below, sensor 10 is alterable between a first conformational state shown on the left side in FIG. 1(a) where the structure of junction 18 substantially impedes charge transfer between the first and second stems 14, 16, and a second conformational state shown on the right side in FIG. 1(b) permitting charge transfer through junction 18 between first and second stems 14, 16. Sensor 10 switches between the first and second conformational states when analyte 12 binds to receptor 20. In other words, the binding of analyte 12 to receptor 20 triggers a conformational change in sensor 10 resulting in a detectable change in charge transfer between first and second stems 14, 16. The conformational change may consist of adaptive folding, compaction, structural stabilization or some other steric modification of junction 18 in response to analyte binding which causes a change in the charge transfer characteristics of sensor 10.

As shown in the embodiment of FIG. 1(a), receptor 20 is physically coupled to junction 18 but does not form a portion thereof. In this embodiment receptor 20 is located proximate to first and second stems 14, 16 but it does not form part of the conductive path in the second conformational state. This is sometimes referred to herein as the "coupled receptor" or "coupled-ligand" embodiment. As shown in the alternative embodiment of FIG. 1(b), receptor 20 may form an integrated portion of junction 18 and hence part of the conductive path between first and second steins 14, 16 in the second conformational state (i.e. when analyte 12 binds to receptor 20). This is sometimes referred to herein as the "integrated receptor" or "integrated ligand" embodiment.

As shown in FIG. 1(a) sensor 10 may also optionally include a third oligonucleotide stem 22. Stem 22 may comprise receptor 20 and may be joined to first and second stems 14, 16 at junction 18. In this embodiment junction 18 therefore consists of a three-way junction. Sensor 10 may also comprise four-way or other multiple stem junctions as described further below.

Sensor 10 further includes a charge flow inducer 24 for controllably inducing charge transfer between first and second stems 14, 16 in the second conformational state. In one embodiment of the invention, the charge flow inducer 24 may comprise a chemical trigger coupled to second stem 16. For example, inducer 24 may consist of a photoexcitable, chemiexcitable or electrochemically excitable moiety which functions as a powerful oxidizing agent in its excited state. By way of example, suitable photoexcitable charge flow inducers 24 may include antraquinone (AQ) or rhodium (III) complexes with aromatic ligands (anthraquinone is shown as a charge flow inducer in the illustrated embodiment). As will be appreciated by a person skilled in the art, inducer 24 could alternatively comprise a powerful reducing agent configured to cause net charge flow (i.e. in the direction opposite to that shown by the arrow in FIGS. 1(a) and 1(b)) when triggered).

Charge transfer within sensor 10 may be detected either directly or indirectly in different embodiments of the invention. As shown in FIG. 1(a), sensor 10 may include a detector 26 coupled to first stem 14 for directly detecting charge transfer between first and second stems 14, 16 in the second conformational state. Detector 26 may comprise, for example, a semi-conductor chip or some other conductive surface for direct current measurements. In one alternative embodiment of the invention, charge flow inducer 24 may be omitted if stems 14, 16 are each directly connected to electrodes or other conductors (not shown) for directly inducing and measuring charge transfer between stems 14, 16.

The use of DNA-based sensors 10 for direct electrical or electrochemical measurements has many potential advantages in the field of gene chip technology. The technology for attaching DNA molecules to gold surfaces has already been worked out and optimized[31]. Direct measurement of differences in charge transfer could be employed to achieve rapid and automated chip-based detection of small molecules as well as of proteins, macromolecules and other analytes 12.

In another embodiment of the invention, charge transfer in the second conformational state may be detected indirectly. For example, inducer 24 may be selected to function, when triggered, as a powerful oxidizing agent causing the formation of oxidation products. As described in detail below, the position of oxidation products along a DNA strand may be detected by sequencing gel-electrophoresis to indirectly detect charge transfer. As mentioned above, one mechanism for explaining the electrical conductivity of double-helical DNA is by means of a "multi-step hopping reaction" whereby guanine residues donate electrons when subjected to oxidization. When triggered, inducer 24 acts as an electron sink capable of collecting electrons from guanines via generation of a mobile radical cation, or electron hole, within the DNA duplex. This effect has been reported at distances exceeding 200 Å away from the ligand[15a,b]). According to the hopping reaction mechanism, the radical cation moves from guanine to guanine (guanine is the base with the lowest ionization potential). A guanine upon which the mobile radical cation is transiently localized is somewhat susceptible to reaction with water and dissolved oxygen, leading to the formation of oxidation products such as diaminooxazalone and 2-aminoimidazalone[16]. The position of the latter products along a DNA strand can readily be detected by sequencing gel-electrophoresis, since these products are base-labile and cause site-specific DNA strand cleavage when treated with hot piperidine. It has been noted, in particular; that stretches of guanines, e.g. GG or GGG on a given strand, are especially susceptible to oxidation, with the 5'-most guanine of these stretches usually the most oxidizable.

It is therefore believed that conduction through a regularly ordered DNA helix (FIG. 2(a)) depends upon (a) the continuity of the π-stacking interactions of the base pairs, and (b) on successive G-C base pairs in the duplex being separated by no more than approximately 2 A-T base pairs. Other considerations apply in the case of more complex structures, such as the sensors 10 of the present invention. As shown in FIG. 2(b), two unpaired nucleotides (i.e. non-Watson-Crick base pairs) may be located at or near junction 18. Guanine electron-donation may be dependent upon the specific conformation of the three-way junction 18. In a standard three-way junction 18 (FIG. 2(c)) steric interference between the three oligonucleotide stems 14, 16, 22 will normally preclude ordered coaxial stacking of any two of the three stems. Therefore the passage of electrons from the guanines (shown as dark stubs in the drawings) of first stem 14 to moiety 26 connected to second stein 16 is less efficient relative to donation by the equivalent guanine in a conventionally ordered double helix. However, the presence of two unpaired nucleotides at or near junction 18 (FIG. 2(a)) does allow a 3-way junction to coaxially stack two of its three stems 14, 16, 22. Variables affecting the efficiency of base pair stacking in the region of junction 18 include the identity of the base pairs at the junction itself as well as reaction conditions, such as the ionic conditions of the solution.

As indicated above, anthraquinone is convenient for use a charge flow inducer 24 since it is a chemically robust entity that is not easily damaged by changes in temperature or pH. However, other such reagents are known (including other organic moieties, as well as various ruthenium and rhodium organometallic complexes containing aromatic ligands capable of intercalating into DNA), that are also suitable as photooxidants.[14] The ruthenium and rhodium complexes, moreover, used together, can be used in a fluorescence-quenching detection method for monitoring charge conduction through DNA.

As will be apparent to a person skilled in the art, different means for directly and indirectly measuring changes in DNA conformation and conductivity are described in the literature and may be used in conjunction with the present invention. Fluorescence methods have traditionally dominated instrumentation for DNA analysis. The disadvantages of fluorescent labeling are cost, linearity, sensitivity and the inherent need for analyte labeling. The detection of electrical properties of DNA through charge transfer reactions is also known in the art. For example, Barton and co-workers have used electrocatalysis to detect single-base mismatches in double-stranded DNA immobilized on a gold electrode surface by means of a thiol tether. Charge-transport through the DNA duplex was detected as it shuttles from a redox-active DNA intercalator (methylene blue) to a redox species (ferricyanide).[21] Direct measurement of current fluctuations on a gold or other metal surface offers an attractive alternative to traditional fluorescence quenching.

The present invention could be adapted for use with other data readout systems for identifying changes in electrical conductivity caused by analyte binding and for amplifying target signals to enhance sensitivity. For example, possible detection strategies include surface-enhanced resonance Raman scattering, surface plasmon resonance methods, acoustic wave sensors, and mass spectral analysis.

As illustrated in FIG. 3(a)-(d), sensor 10 may comprise a composite of different forms of nucleic acids in some embodiments of the invention (e.g. DNA, RNA and other modified or synthetic nucleotides). In the cell, DNA is found essentially in a double-helical form (except in specialized elements, such as telomeres), whereas cellular RNAs are found in a wide variety of complexly folded shapes. Consequently, too, there is a larger variety of modes of protein-RNA interaction found in nature, relative to modes of DNA-protein interaction. In addition, in vitro selection experiments have been carried out for a substantially larger number of RNA aptamers than DNA aptamers (although individual RNA and DNA aptamers are often of comparable quality, complexity, and ligand-binding affinity)[14]. The large number of naturally occurring binding sites and aptamers made of RNA may be exploited in the design of sensors 10. For example, sensors 10 may be formed wholly from RNA, in which case charge conduction occurs through double-helical RNA. In modular sensors 10 a wholly DNA conduction path (i.e. oligonucleotides 14, 16) is coupled to a wholly RNA receptor 20. In mixed sensors 10 the conducting path itself (i.e. oligonucleotides 14, 16) may comprise a RNA-DNA heteroduplex (FIGS. 3(a) and 3(b)).

As will be appreciated by a person skilled in the art, indirect detection of charge transfer in oligonucleotide stems 14, 16 comprising RNA double helices may require different protocols than double-stranded DNA. As described above, oxidation damage at specific guanines in DNA is generally observed by heating DNA with piperidine, a process that leads to strand cleavage at the damaged guanines. With RNA, however, this procedure cannot be used, since RNA will be hydrolyzed non-specifically by hot piperidine solutions. As an alternative, RNA double helices (in which one strand has been covalently derivatized at its 5' end to a charge flow inducer 24, such as an anthraquinone moiety), may be treated with borohydride followed by hot aniline. This protocol is used to generate a dimethylsulfate G-ladder[22] for RNA, and it is expected that it will work similarly to detect oxidation products of guanines derived from RNA double helices. Of course, other direct or indirect charge transfer detection means could be employed as discussed above in the context of DNA double helices.

Sensors 10 constructed from RNA stems 14, 16, 22 and receptors 20 may be useful for the detection of specific types of RNA-binding analytes 12, such as HIV Rev proteins. The small HIV-coded proteins, Tat and Rev, are among the best characterized of all RNA-binding proteins[23]. Their function is to bind to specific binding sites in the HIV genomic RNA (at the TAR and RRE RNA loops), and the binding of both proteins is crucial for the HIV life-cycle[23]. In structural terms, the binding of Tat to TAR and Rev to RRE, have the property of causing adaptive folding of these RNA loops to compact and stacked structures. High resolution NMR structures of both the TAR[24] and RRE[25] RNAs (with and without bound protein) have indicated induced-fit folding of these RNA loops. The binding of Rev to RRE, in particular results in the closing of a large, and largely unstructured, bulge into a tightly hydrogen-bonded and stacked structures. This RRE loop will, therefore, lend itself to incorporation into an RNA sensor 10, for use as a receptor 20 of the HIV Rev protein analyte 12.

The inventors have obtained a clone for HIV Rev, and purification of this protein is fairly simple. The RNA for constructing the sensors 10 may be obtained using the in vitro T7 RNA polymerase system for underivatized RNAs, and from chemical synthesis (where the RNA needs to be derivatized with anthraquinone).

FIGS. 3(a) and 3(b) illustrate modular RNA sensors incorporating RNA-DNA chimaeric stems 14, 16. Mixed sensors 10 comprising a simple RNA/DNA heteroduplex are shown. A study on such heteroduplexes has recently been carried out by Barton[26], and it has been found that they do indeed conduct charge similarly to DNA[26]. The advantage of using RNA-DNA heteroduplexes (relative to duplex RNA) is that the guanines used for monitoring conduction can all be placed on the DNA strand and, hence, standard hot piperidine treatment can be carried out to detect oxidative damage to these guanines.

Depending upon the application, receptors 20 comprising RNA aptamers may be more effective in binding a target analyte 12 than DNA aptamers. However, the sensitivity of detection may be dependent upon other factors as well, such as the "conformational information transmission" properties of the linking element (i.e. the structure or "communication module" connecting receptor 20 to the 3-way junction 18 and to the conducting stems 14, 16).

As indicated above, sensors 20 may comprise a fourth or other supplementary oligonucleotide stem 28 which is joined to stems 14, 16 and 22 at a 4-way junction 18 (FIGS. 3(c) and 3(d)). The properties and conformational transitions of 4-way helical junctions 18 (immobile Holliday Junctions) have been studied extensively, using a wide variety of techniques (reviewed in ref. 26a), and their conformational properties are, on the whole, better understood than those of 3-way junctions 18. Unlike 3-way junctions, in which, depending on the context, two of the three (or none of the three) stems 14, 16, 22 may stack with each other (and, with different degrees of colinearity), 4-way junctions 18 typically adopt a standard stacked geometry under physiological salt conditions, with the four stems 14, 16, 22, 28 stacking up in pairs to give an X-shaped structure (shown in two dimensions as an 'H' shape in FIGS. 3(c) and 3(d), right). The choice of which 14, 16, 22, 28 stacks with which other is significantly determined by the identity of the base-pairs at the junction itself. Under low-salt conditions, however, 4-way junctions adopt an opened up, cross-shaped conformation (FIGS. 3(c) and 3(d), left) with minimal stacking between the four stems 14, 16, 22, 28.

In accordance with one embodiment of the invention, sensor 10 may be configured so that one of the four stems (e.g. stem 22 in FIGS. 3(c) and 3(d)) is a relatively unstructured receptor 20. According to this design, junction 18, in the absence of added analyte 12, will adopt a looser structure than the tight X-structure of authentic 4-way junctions (i.e. resembling the looser structure shown in FIGS. 3(c) and 3(d), left). The binding of analyte 12 to receptor 20, however, should fold that bulge into a helix-like stem; and, the presence, now, of this additional stem, should favour the formation of the classic X-shape. In such a design, one of the three preexisting stems of the junction would be designated the first or detector stem 14—its identity empirically determined as that stem most responsive—in terms of enhanced charge conduction through its guanines—to binding of analyte 12.

Depending upon their configuration, 4-way junction-based sensors 10 may provide sharply differentiated yes/no responses to the presence of analyte (given their propensity of 4-way junctions 18 to exist in one of two states—stacked or unstacked). It is also possible that better signal-to-noise ratios may be achieved with 4-way junction sensors 10 than with their 3-way junction counterparts. As will be appreciated by a person skilled in the art, five-way or higher number junctions 18 may be similarly employed in embodiments of the invention where more complex switching functionalities are desirable.

Figure 4A:
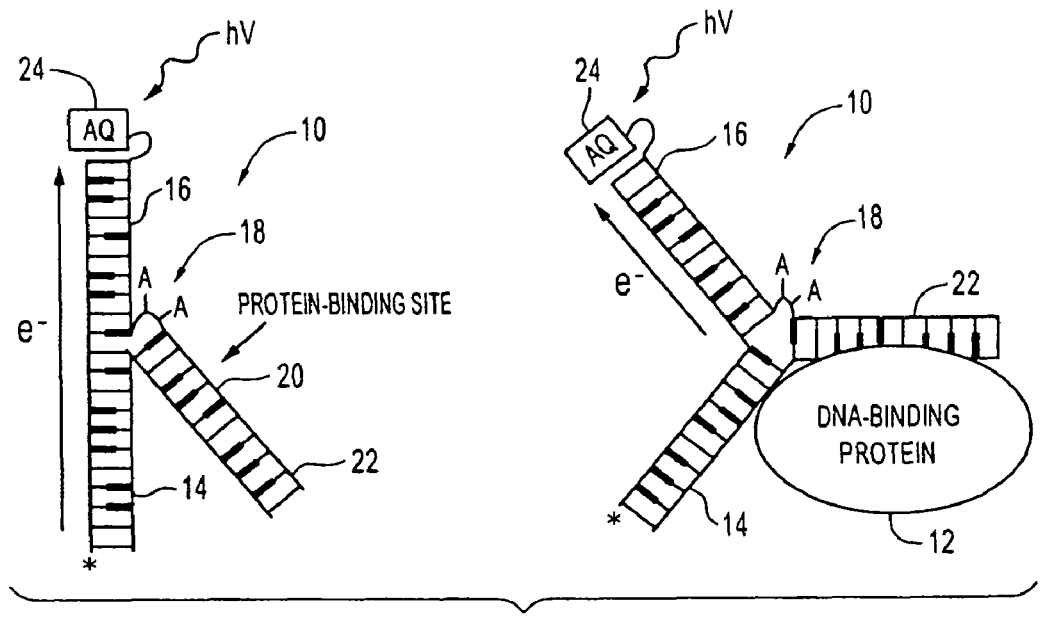
FIG. 4(a) is a schematic view of a protein-detecting sensor illustrating detection by physical interference.
Figure 4B:
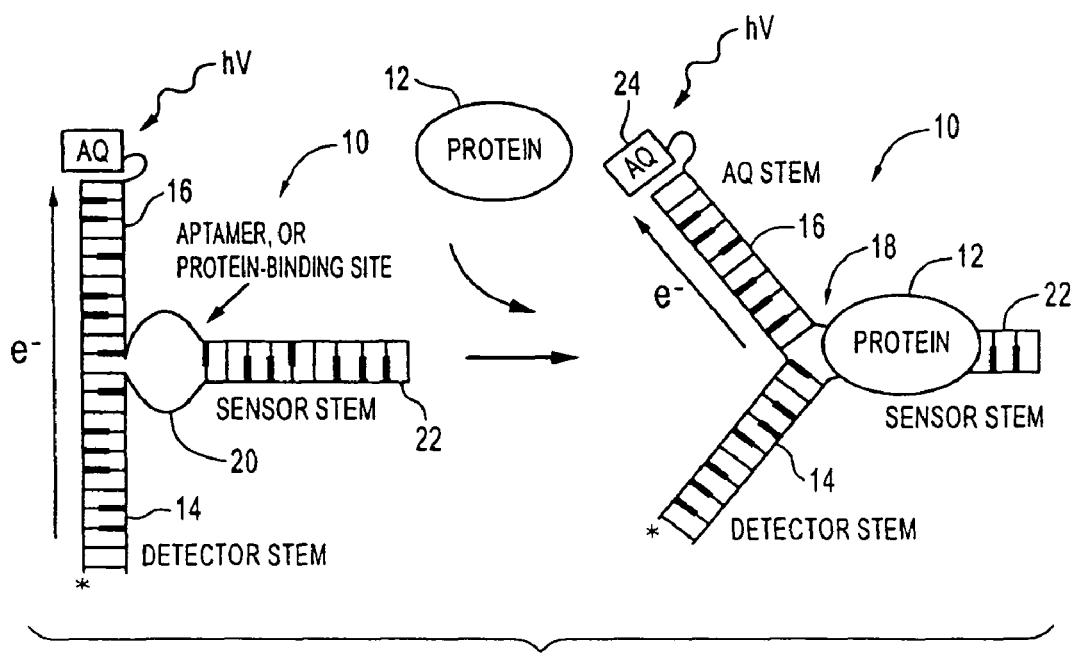
FIG. 4(b) is a schematic view of a protein-detecting sensor illustrating detection by adaptive binding.

As shown in FIGS. 4(a) and 4(b), sensors 10 may be specifically configured to detect protein analytes 12. In one mode, binding of the protein analyte 12 to receptor 20 physically intefers with the electronic path between stems 14, 16 (and hence is detectable as reduction in charge transfer). In a second mode, the protein analyte binds to receptor 20, which may comprise a complexly structured DNA or RNA binding site, and cause an adaptive tightening and stabilization of that binding site (which, in turn, can be transmitted to stabilize or improve the charge conduction path).

FIG. 4(a) illustrates the binding of a relatively large protein analyte 12 to either its natural binding site (for a DNA-binding protein) or to an aptamer element (for a non-DNA-binding protein) located at receptor 20 on stem 22. In this embodiment receptor 20 is located proximate to 3-way junction 18. Binding of the protein analyte 12 to receptor 20 could, by a process of physical interference by the protein (if the protein were bulky enough and positioned correctly with respect to the 3-way junction 18), alter the stacking geometry and, hence, the conduction path between stems 14, 16. Naturally DNA-binding proteins, including transcription factors such as the TATA-binding protein, glucocorticoid receptor proteins, GAL4 from yeast, or CAP or the lac repressor from E. coli could be suitable, for example, for this sort of detection. As will be appreciated to a person skilled in the art, the specific location and orientation of receptor 20 on stem 22 (such as its distance from junction 18 and its position along the helical path of the stem) could be selected to ensure a steric clash of the bound protein with the first and second stems 14, 16.

The sensor design shown in FIG. 4(a) is configured to detect the binding of the cognate protein analyte 12 by a net decrease of charge flow through stems 14, 16. Alternatively sensor 10 could be configured to yield an increase in current upon analyte binding. This may necessitate-starting out with a different design of 3-way junction 18, perhaps such that the second stem 16 is initially stacked with the third stem 22 (containing receptor 20) rather than the first stem 14.

Another potential way to detect the binding of certain protein analytes 12 (ideally, smaller proteins) might be on the basis of the adaptive folding of their RNA and DNA binding site(s) on receptor 20 (FIG. 4(b)). In exhibiting such binding behaviour, these proteins would functionally resemble the small molecule analytes 12 (discussed above).

Figure 5:
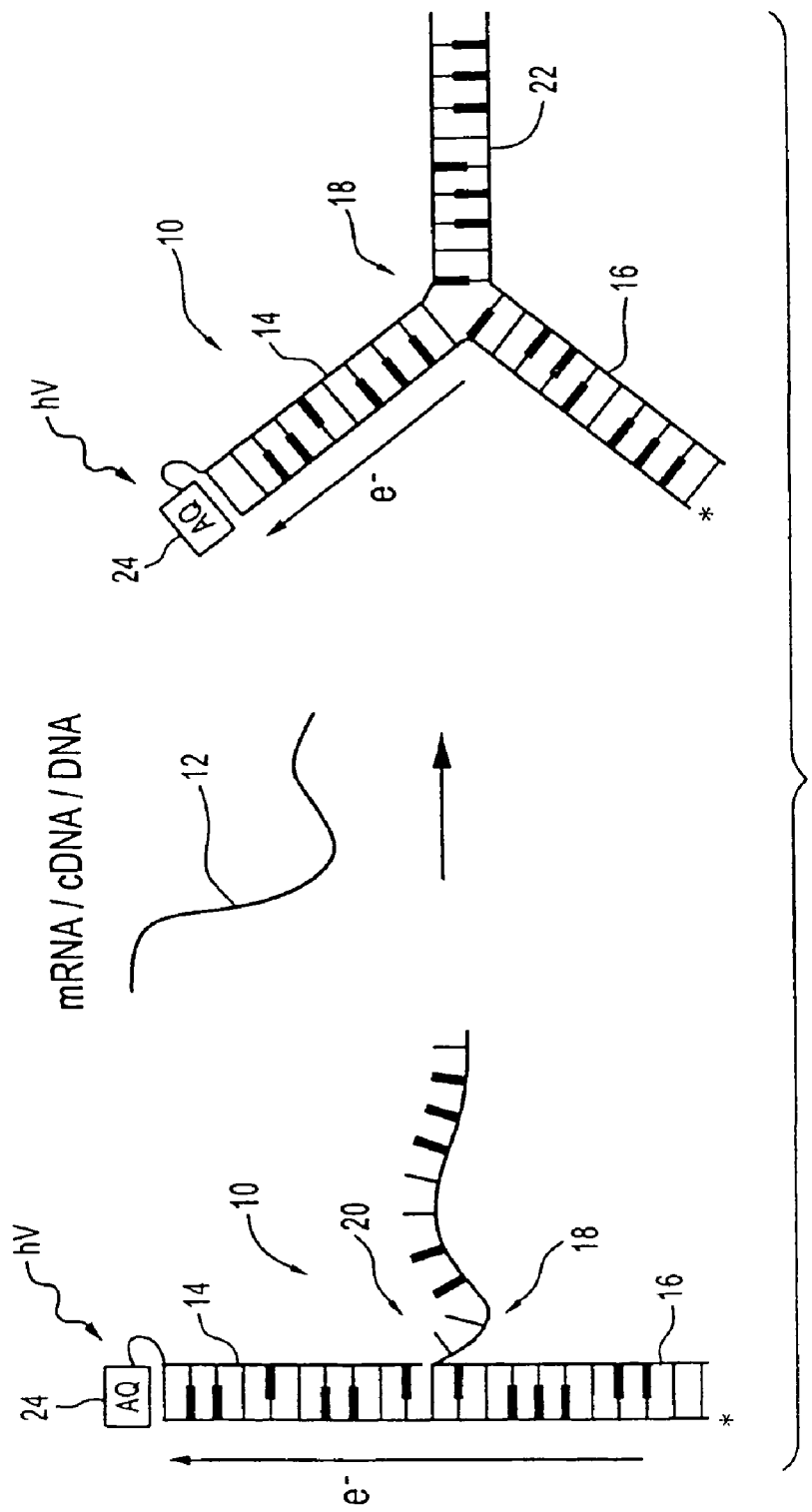
FIG. 5 is a schematic view of sensor configured to detect nucleic acids.

FIG. 5 illustrates an embodiment of the invention for use in binding and detection of nucleic acid analytes 12 (i.e. DNA or RNA oligomers). In this embodiment incomplete 3-way junctions 18 will be constructed, which will incorporate two complete stems 14, 16, coaxially stacked, as well as one of the two strands of a potential third stem 22. This dangling single-strand stem 22 would, essentially function as a receptor 20 for its complementary nucleotide sequence. In principle, the binding of an oligonucleotide of the correct length and with the correct complementarity to the dangling single-strand stem 22 (under defined conditions of hybridization) would complete a strained 3-way junction 18 (FIG. 5). In the illustrated embodiment, this results in the introduction of an enhanced steric strain in junction 18. The poor stacking of helical stems 14, 16 in such a strained junction 18 (i.e. in the second conformational state) would lead to poorer conduction in first stem 14 relative to its more orderly stacked precursor (in the first conformational state). The single-stranded element comprising receptor 20, 15-18 nucleotides long, could in principle have any sequence or length, although the illustrated embodiment is on the order of 15-18 nucleotides long. Receptor 20 could even represent a collection of sequences to make up a library sufficient to specify every 15-18-nucleotide stretch of sequence present within a $^-10^9$ base pair genome.

The present invention also has potential application as a DNA conductor used in gene chips. Such chips typically consist of arrays of single-stranded oligomers; which are poor conductors. When, however, a complementary strand hybridizes to a given oligomer on the chip, that newly-formed double helix can be detected by virtue of its superior conductivity. This is an interesting conception; however the conductivity of individual double helices formed in this way will vary widely (depending on the guanine-content of the duplex, and the location of those guanines relative to one another). In other words, the electrical signal measured will vary, depending on what duplex has been produced, and this may give rise to ambiguity as to whether a positive (i.e. hybridization) signal is being observed or not.

One advantage of Applicant's invention as described above is that the two stacked stems 14, 16 making up the charge flow path could remain constant for the entire library and hence a clear signal will be generated for every single case of hybridization of a target analyte 12 to a receptor 20, for example located on a third stem 22. Thus, a hybridization event to a receptor 20 of any sequence should produce a standard conductivity enhancement (or decrease, as the case may be) in the conduction path as the sensor switches between the first and second conformational states.

As will be apparent to a person skilled in the art, various enhancements and modifications to the DNA/RNA conductor backbone and switching configurations of sensors 10 are possible without departing from the invention. For example, as indicated above, the structure of the nucleotide stems 14, 16, 22 and aptamer sequences at receptor site 20 may be varied to include non-naturally occurring molecules, including nucleic acid analogues and nucleic acid-like molecules capable of base pairing. The synthesis and properties of modified oligonucleotides has been described in the literature (e.g. Modified oligonucleotides—synthesis, properties and applications, Iyer et al., Current Opinion in Molecular Therapeutics (1999) 1(3):344-358; Backbone Modification of Nucleic Acids: Synthesis, Structure and Therapeutic Applications, Micklefield, Current Medicinal Chemistry, 2001, 8, 1157-1159, the text of which is incorporated herein by reference). Synthetic oligonucleotides could be configured, for example, to increase stability to enzymatic degradation, enhance affinity for binding to target analytes 12 or to optimize electrical conductivity.

Figure 6:
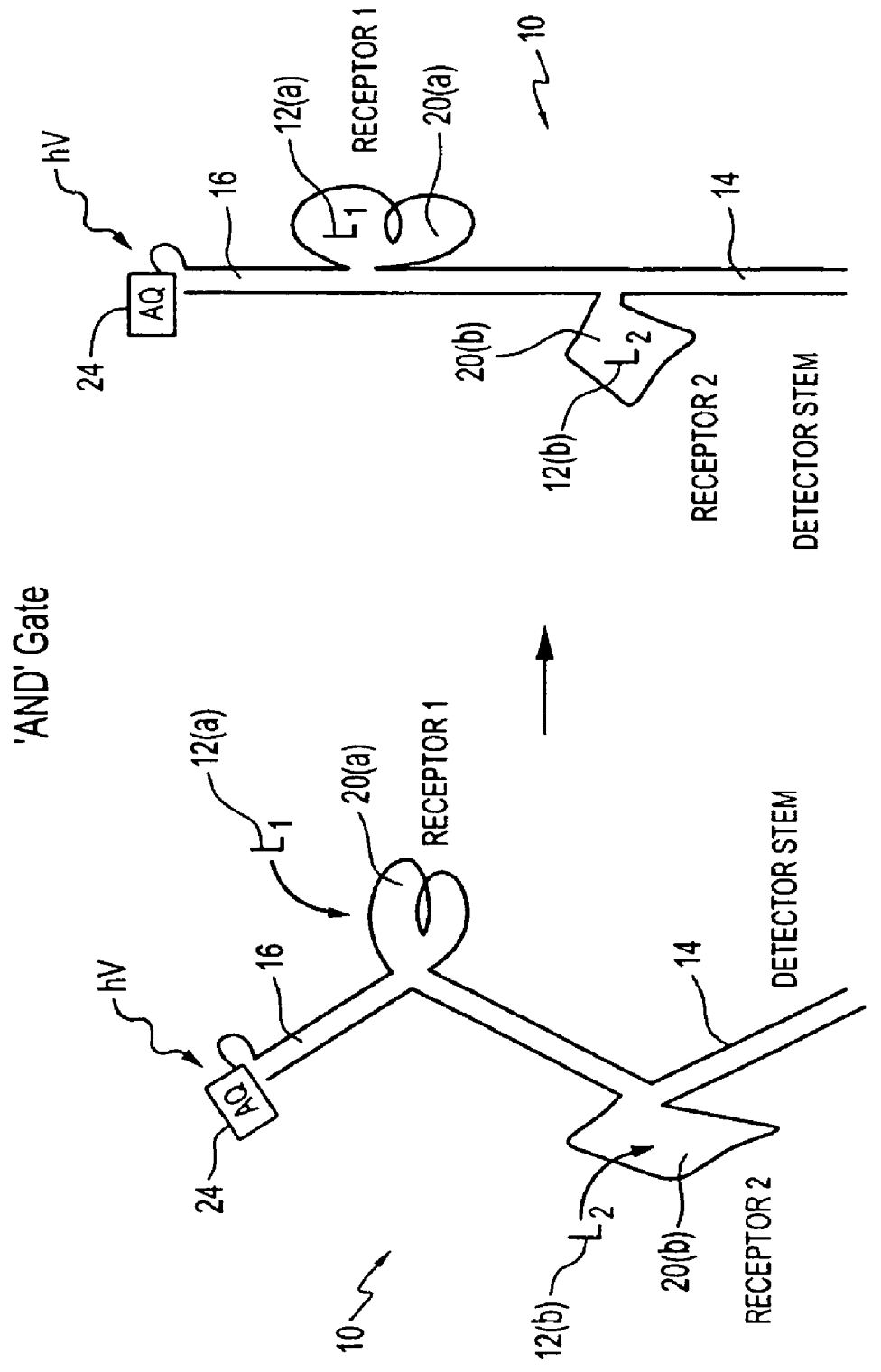
FIG. 6 is a schematic view of a sensor designed to simulate an "AND" logic gate.

Sensors 10 of the present invention are also potentially useful as nanoelectronic switches and junction devices simulating solid state electronic logic gates. As shown in FIGS. 6-9, each DNA sensor 10 is operable in one of two distinct states (e.g. "on" or "off" or "conducting" or "non-conducting"). FIG. 6 shows an "AND" logic gate. As in several of the other embodiments described, a charge flow inducer 24, such as the oxidant anthraquinone "AQ", is tethered covalently to the end of a second stein 16. A pair of receptors 20(a) and 20(b) are disposed between the first and second stems 14, 16. In order to achieve electron flow in this embodiment between stems 14, 16, both of analytes 12(a) and 12(b) must bind to their respective receptors 20(a) and 20(b). That is, binding of only one analyte 12(a), 12(b) is not sufficient to trigger electron flow between stems 14, 16.

Figure 7:
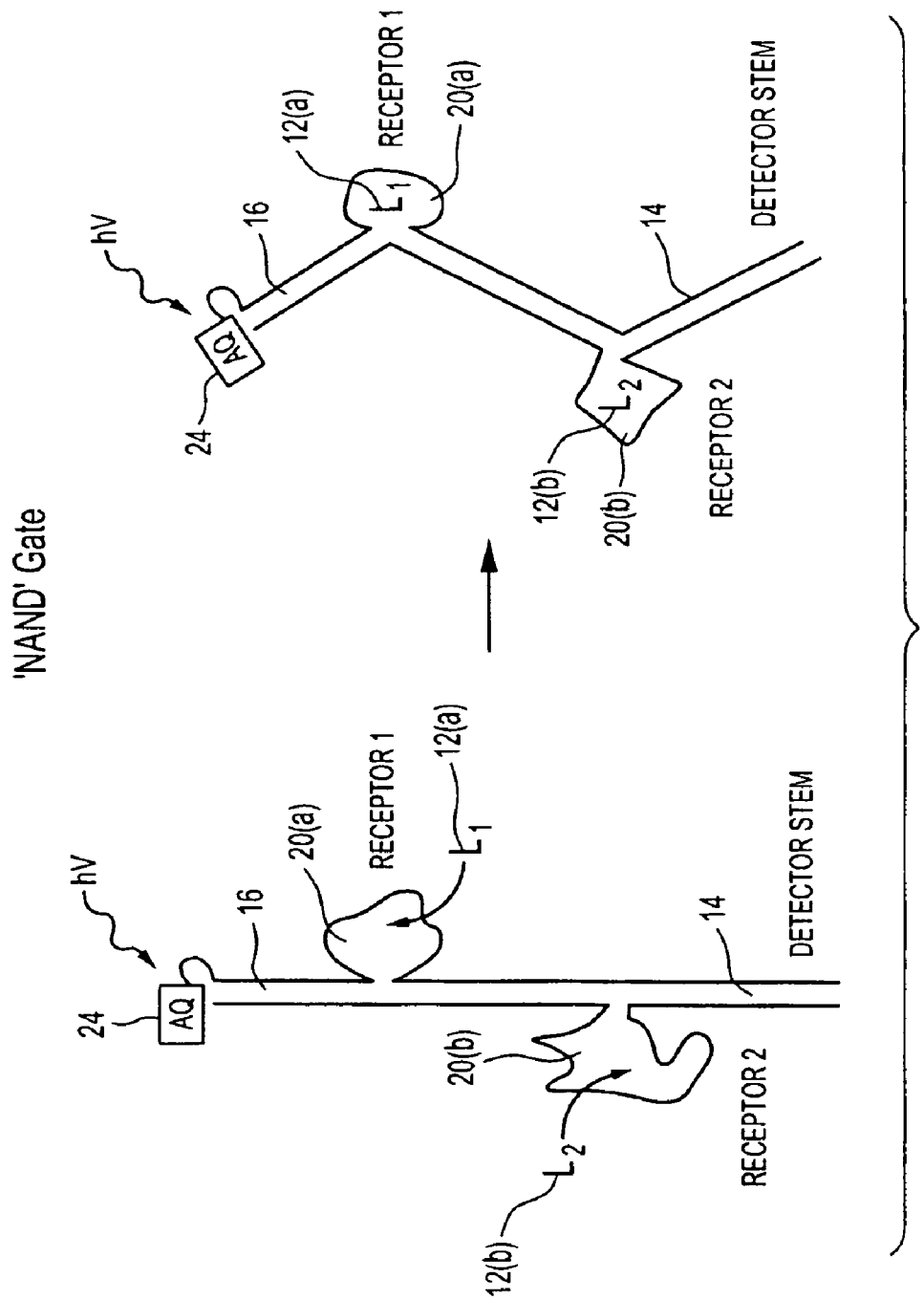
FIG. 7 is a schematic view of a sensor designed to simulate a "NAND" logic gate.

FIG. 7 shows a "NAND" logic gate. In the "NAND" gate embodiment receptors 20(a) and 20(b) are configured to ordinarily not interrupt electron flow between the first and second stems 14, 16. However, when both of analytes 12(a) and 12(b) bind to their respective receptors, stems 14, 16 undergo a conformational change resulting in cessation or a reduction in electron flow (e.g. sensor 10 switches from the first to the second conformational state). As will be appreciated by a person skilled in the art, other logic gate configurations employing coupled receptor sensors 20 could be chosen, such as "OR", "NOT", depending upon the functionality required.

Figure 8:
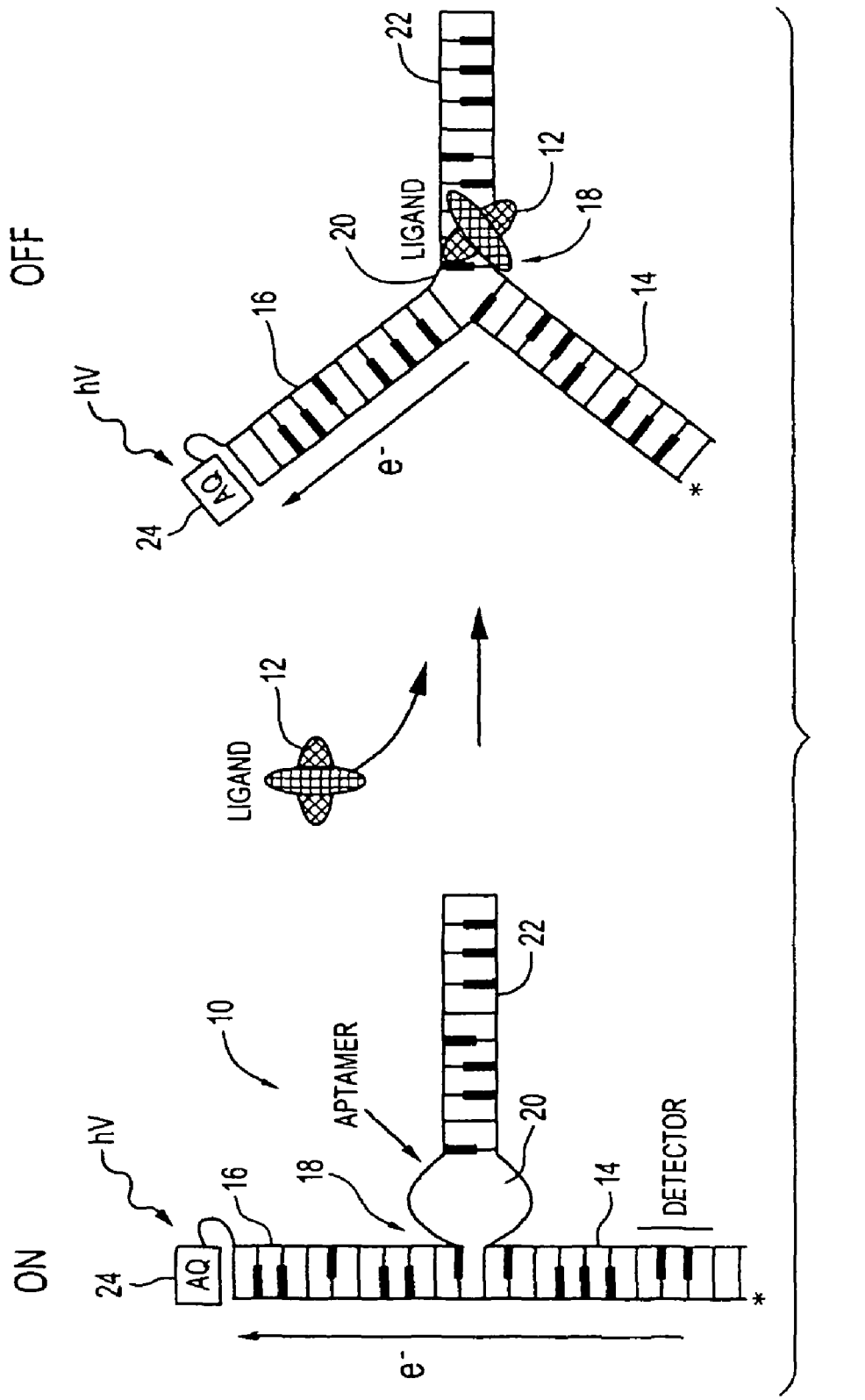
FIG. 8 shows a sensor which may be switched from an "ON" to an "OFF" logic state upon binding of a target analyte.
Figure 9:
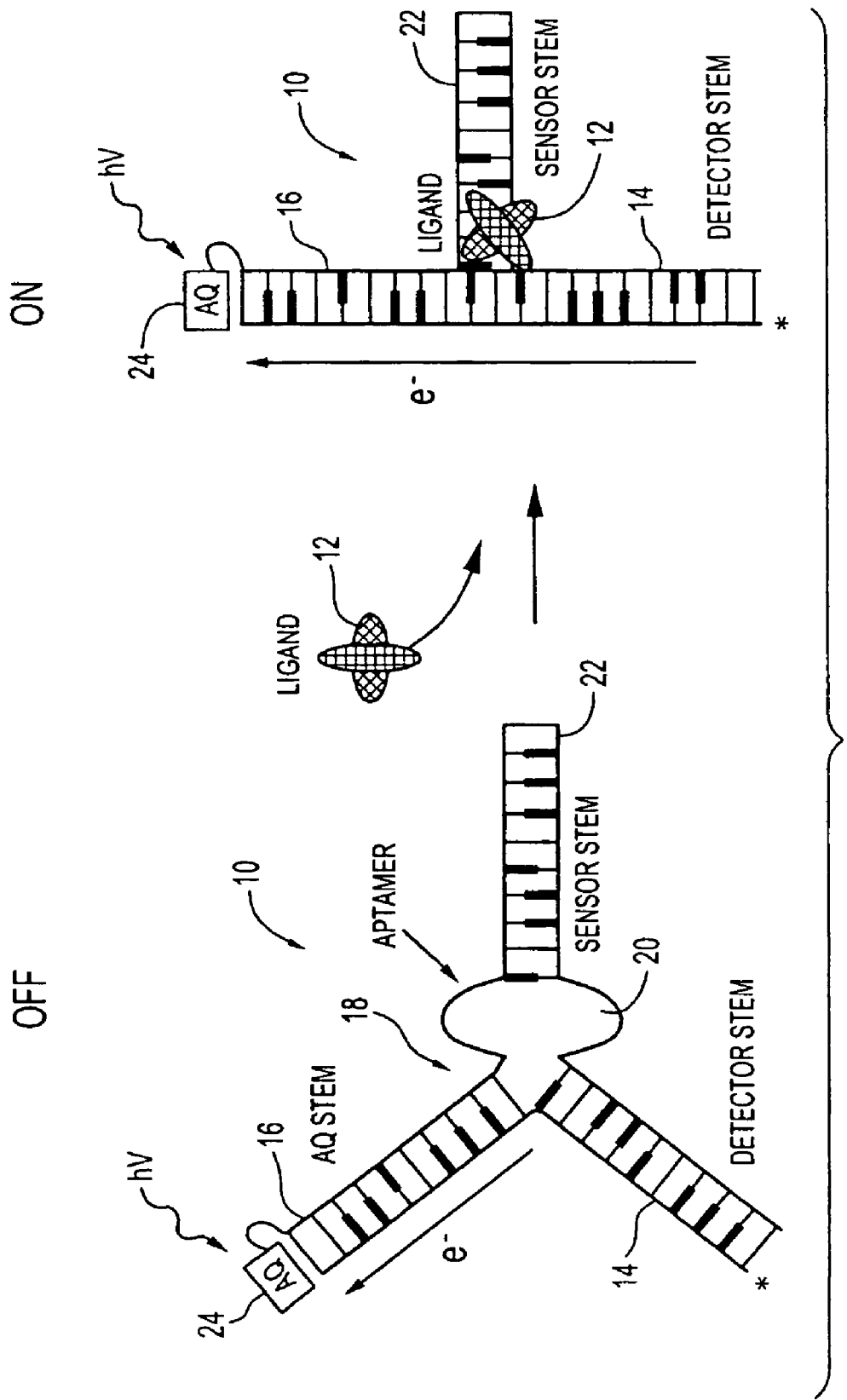
FIG. 9 shows a sensor which may be switched from an "OFF" to an "ON" logic state upon binding of a target analyte.

FIGS. 8-9 and illustrate a similar concept employing a single coupled receptor sensor 10 disposed at junction 18 between first, second and third stems 14, 16 and 22. In FIG. 8 the gate is ordinarily "ON" but may be switched "OFF" upon the binding of analyte 12 which alters the conformation of at least some of stems 14, 16, 22 at three-way junction 18. The opposite configuration is shown in FIG. 9. That is, the logic gate is ordinarily "OFF" but may be switched "ON" upon the binding of analyte 12. These examples highlight the versatility and scalability of the coupled receptor sensor/switch concept described herein (i.e. where analyte binding event(s) are transformed into electrical signal(s)).

Figure 10:
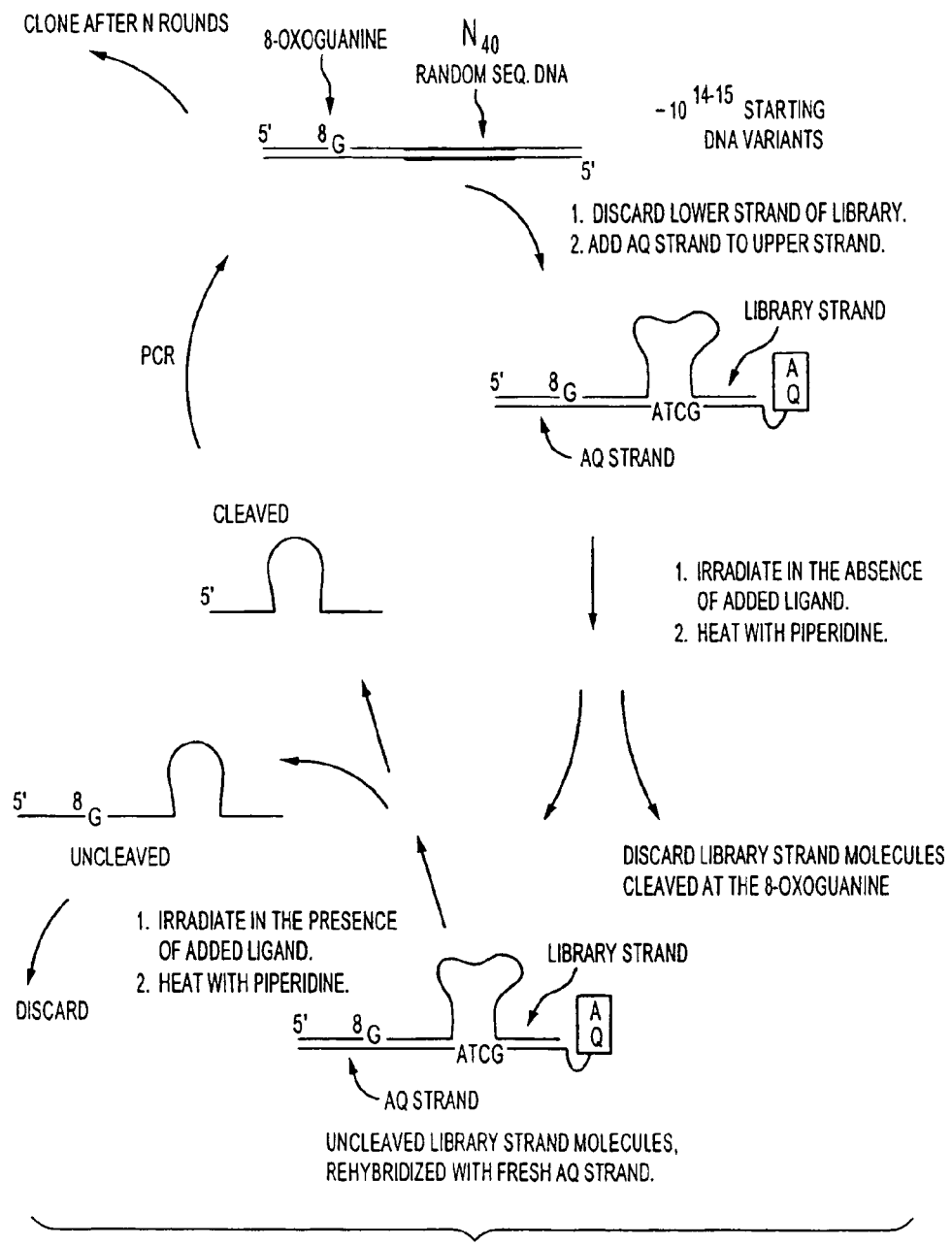
FIG. 10 is a schematic view of a process for in vitro selection of sensors specific for a particular target analyte.

FIG. 10 illustrates an in vitro selection protocol approach for rationally designing sensors 10 for different categories of small molecules and macromolecules or other analytes 12. The protocol may be potentially employed to select receptors 20 for any molecule (regardless of whether there exists any natural RNA/DNA binding site for such a molecule or, indeed, an aptamer).

FIG. 10 shows the design of a random sequence-containing library of $10^{14-15}$ individual sequences, and a scheme for the selection of receptors 20, to be carried out in the solution phase (as opposed to being immobilized on a column). A random sequence duplex DNA library (FIG. 10, top), containing an $N_{40}$ random sequence region as well as a single 8-oxoguanine ($^8$G) residue (a highly oxidizable base analogue[27], superior to guanine, but too expensive to use routinely) in one of the two strands, will be treated in a standard fashion to obtain the $^8$G-containing strand as a single strand (the protocol for doing this involves immobilizing the duplex onto an avidin column using a single biotin attached to the non-$^8$G-containing strand, and then eluting off the other strand with a 0.2N sodium hydroxide solution). The single-stranded library so obtained will be hybridized to a fixed-sequence, partially complementary, AQ strand (i.e. the second stem 16), containing a covalently attached anthraquinone residue on its 5' end. The hybridization of the library strand with the second stem 16 should give rise to a partial heteroduplex (FIG. 10, right), in which the $N_{40}$ element is looped out. It is anticipated, based on prior experience in the field, that aptamer- or receptor binding-elements for particular analytes will emerge out of this $N_{40}$ element during the cycles of selection.

The following, then, are the detailed features of this starting DNA complex (FIG. 10, right) for our selections: the AQ strand, 45 nucleotides long, and of predetermined sequence, will have at its 5' end a covalently tethered anthraquinone (AQ) moiety. The other strand (the "random strand"), 80 nucleotides long, will have, as its 5' and 3' extremities, a 15-nucleotide and a 25-nucleotide fixed sequence stretches, fully complementary to the AQ strand. In die remaining 40 nucleotides of this random strand ($N_{40}$) each nucleotide position will have an equal probability of being an A, C, C, or T (tie generation of such random-sequence stretches within synthetic DNA molecules is routinely achieved by automated synthesis). The "random" strand will also be $^{32}$P-labelled at its 5' end, and will feature the single 8-oxoguanine residue, located 10 nucleotides away from the 5' end.

FIG. 10 shows how the binding of a chosen analyte (i.e. ligand) to one or more individual sequences within the $N_{40}$ element (that might constitute a binding site, or aptamer, for it)—may lead to an adaptive folding of this binding sequence, in turn leading to an aligning and stacking of the first and second stems 14, 16, enhancing the current flow through them (with enhanced oxidative damage to the 8-oxoguanine residue). In other words, the tight binding of analyte to one or more individual members of the 'random' DNA constructs, might, at least in a proportion of cases, lead to enchanced oxidative damage to the 8-oxoguanine residue within those constructs. Heating with piperidine will then break these oxidized strands, shortening them by 10 nucleotides relative to unoxidized strands. These shortened strands can easily be separated and purified by gel electrophoresis, recovered, and re-converted, using PCR, to full-length random strands to be used for the next round of selection.

In carrying-out such a selection we will have to take certain key precautions: (a) the unirradiated "random strand" library will need to be pre-heated (prior to the first round of selection) with piperidine, to eliminate DNA strands that have collected lesions during automated DNA synthesis. Such a pre-treatment with piperidine, in the absence of prior oxidation, should not harm the 8-oxoguanine residue, which is relatively insensitive to piperidine. However, if this pre-treatment leads to a high 'background' cleavage at the 8-oxoguanine, we can switch to GG or GGG sequences to replace the 8-oxoguanine in our library design. (b) Stringent negative selections (i.e. in the absence of added analyte) will be carried out, to element random sequences that contribute to enhanced current flow along the first and second stems even in the absence of added analyte.

A feature of the design shown in FIG. 10 is the presence of four ostensibly unpaired nucleotides (GCTA) at the centre of the second stem 16. These will permit a degree of flexibility in the choice of junction base pairs by emerging 3-way junction sensors during selection.

2.0 Examples

2.1 Example Synopsis

FIGS. 11-15 illustrate an illustrative embodiment of the invention for detecting the presence of the analyte adenosine, which binds poorly, if at all, to double-stranded DNA but for which a high-affinity ($K_d^-$ µM) DNA aptamer sequence has been derived[28]. NMR studies have confirmed that this aptamer, upon binding two molecules of adenosine, shows a typical adaptive folding, forming a tightly hydrogen-bonded and stacked helical structure. Accordingly, in this example, analyte 12 is adenosine and receptor 20 is the adenosine aptamer sequence. Antraquinone is used as a charge flow inducer 24, namely a photoexcitable moiety covalently coupled to second stem 16 for controllably inducing charge transfer.

2.2 Materials and Methods 2.2.1 DNA Preparation.

Unmodified DNA sequences were purchased from Sigma-Genosys and purified by PAGE before use. Sequences to be $^{32}$P-end-labeled were pre-treated with 10% piperidine (90° C. for 30 minutes followed by lyophilization) prior to 5'-$^{32}$P-kinasing and PAGE purification. Such a pre-treatment cleaved DNA molecules damaged during synthesis, leading in turn to lower background cleavages from photo-irradiation experiments, as previously described[30].

DNA sequences to be derivatized with anthraquinone were synthesized with a commercially available 5'-C6-amino functionality, and were purchased from the University of Calgary Core DNA Services. Generation of anthraquinone-modified DNA sequences was accomplished by reacting the N-hydroxysuccinimide ester of anthraquinone-2-carboxylic acid[31] with the 5'-C6-amino functionality on the DNA. Coupling and purification protocols were as described for amine reactive dyes by Molecular Probes[32] with some modifications.

Prior to coupling, the DNA was treated to remove nitrogenous contaminants from the DNA synthesis procedures. The dried DNA samples were first suspended in 100 µl ddH2O, and were extracted three times with 100 µl of chloroform. The DNA remaining in the aqueous phase was then precipitated by the addition of 30 µl 1M NaCl and 340 µl 100% EtOH. Following mixing, the sample was chilled on dry ice for ⁻10 minutes, and then centrifuged in a microfuge for 20 minutes to pellet the DNA. The pellet was washed once with 150 µl of 70% aqueous ethanol (v/v). Following air-drying the pellet was dissolved in 100 µl ddH$_2$O, the DNA concentration of the solution was determined in a standard fashion using UV absorbance measurements.

The AQ-NHS ester (4.8 mg) was dissolved in 238 µl dimethylformamide. For each coupling reaction, 7 µl of this stock suspension was added to 75 µl of a 100 mM sodium borate solution (pH 8.5). To the resulting mixture was added 8-15 µl (5-10 nmoles) of the purified amino-labeled DNA. The tubes containing the coupling mixtures were covered in aluminum foil and shaken overnight at room temperature. The DNA was then ethanol precipitated by addition of 27 µl of 1M NaCl and 280 µl of 100% ethanol (the solution was chilled in dry ice and the precipitated DNA collected and washed as described above). The large pellet obtained (containing a significant amount of the uncoupled anthraquinone) was now suspended in 50 µl of 100 mM aqeous triethylamine acetate (pH 6.9), to which was added 100 µl chloroform. The uncoupled anthraquinone partititioned into the chloroform phase, and the aqueous phase was now extracted two more times with 100 µl chloroform, prior to partial drying under vacuum to remove any residual chloroform. The DNA obtained was then purified by reverse phase chromatography on an HPLC using a C18 Bondapack column (Waters).

The HPLC protocol was as follows. The solvent flow was continuous at 1 ml/minute, and the column was heated to 65° C. The initial conditions were: 100% Solvent A (20:1 of 100 mM triethylamine acetate, pH 6.9: acetonitrile) changing to 30% Solvent B (100% acetonitrile), over 30 minutes and with a linear gradient. After this period, the solvent was rapidly changed to 100% Solvent B, for 15 minutes, before reconditioning the column to the starting conditions.

The concentrations of the various products of the coupling reactions could be determined spectroscopically. Absorbance values for the conjugate were made at 260 nm, using extinction coefficients for the individual bases obtained for single stranded DNA. $\epsilon$ (260 nm, $M^{-1}cm^{-1}$): adenine (A)=15,000; guanine (G)=12,300; cytosine (C)=7,400; thymine (T)=6.700; and, anthraquinone (AQ)=29,000. Typical yields of AQ-DNA conjugates ranged from 50-85% depending on the sequence of the DNA oligonucleotide being coupled, and the synthetic batch.

2.2.2 Preparation of DNA Assemblies.

DNA assemblies were formed by annealing mixtures of constituent DNA oligonucleotides (1 µM each) in 100 mM Tris-Cl, pH 7.9, and 0.2 mM EDTA. DNA solutions were heated to 90° C. for 2 minutes, and then cooled at a rate of 2° C./minute to a final temperature of 20° C. The solutions were then diluted two-fold with either 5 mM $MgCl_2$, or with 5 mM $MgCl_2$ and 200 mM NaCl (the final solutions being defined as the 'Mg' and 'Mg—Na' buffers, respectively). These solutions also contained 2× concentrations of adenosine or uridine in some samples. After mixing, the samples were incubated for approximately 30 minutes at room temperature before photo-irradiation.

2.2.3 Photo-Irradiation.

Pre-incubated samples were placed under a UVP Black-Ray UVL-56 lamp (366 nm peak intensity, at 18 W) for 90 minutes at a distance of 4 cm from the bulb. Temperature was maintained by having the samples tubes placed in a water bath set to the desired temperature. Following photo-irradiation, the samples were lyophilized, and then treated with hot piperidine as described above. The treated DNA samples were then loaded on 11-12% sequencing gels and analyzed using a BioRad Phosophorimager.

2.3 Results

2.3.1 The Integrated-Ligand Sensor.

Experimentally, the most sensitive way to monitor changes in electrical conductivity at the level of individual nucleotides is to electrophoretically monitor DNA strand cleavage resulting from base-labile oxidative damage suffered by individual guanines[33]. This method of monitoring charge transport, often termed "water trapping", has been successfully used to monitor the long-range effects (>150 Å)[34-35a] of a variety of oxidant groups covalently attached at defined sites on the DNA (reviewed by Grinstaff[35b]). FIG. 12 shows the DNA sequences and schematic of a potential "integrated" adenosine sensor, and of a "control" Watson-Crick duplex construct (the $^{32}$P-labeled strand is identical in the two constructs). The 5' $^{32}$P-labeled strands in the constructs contain guanine doublets (GG) on either side of the ATP aptamer domain (or its Watson-Crick base-paired counterpart). The proximal ("P") guanine doublet allows convenient monitoring of charge transfer in the second (i.e. AQ stem) 16, while the distal ("D") doublet permits the same for the first (i.e. detector) stem 14. Guanine doublets have been used in preference to isolated single guanines for charge transfer measurements because of the former's higher reactivity (particularly that of the 5' guanine) in water trapping experiments[36]. The particular base composition of the duplex immediately adjacent to the AQ-tether was chosen because this sequence has been shown to promote efficient charge transfer from the tethered and photo-excited anthraquinone[37].

Upon photo-irradiation at 366 nm wavelength in Mg—Na buffer (50 mM Tris-Cl, pH 7.9, 2.5 mM MgCl$_2$, 100 mM NaCl and 0.1 mM EDTA), the anthraquinone-modified DNA constructs shown in FIG. 12 showed distinctive oxidative cleavage patterns. Both the control duplex and the integrated-ligand sensor 10 exhibited significant levels of strand cleavage at the proximal ("P") guanine doublet in the presence of 2.5 mM adenosine (FIG. 13(a), lanes 5 and 12), 2.5 mM uridine (lanes 6 and 13) or no added nucleoside (lanes 4 and 11), relative to the 'dark' (or, unirradiated—lanes 3 and 10) controls. Dramatic differences between the constructs, however were observed in cleavage at the distal ("D") guanine doublet. In both the presence and absence of added nucleosides the control duplex exhibited identical levels of cleavage at the "D" guanines (lanes 4-6). However, the integrated-ligand sensor only exhibited significant cleavage at the "D" guanines in the presence of adenosine (lane 12), but not in the presence of uridine (lane 13), no added nucleoside (lane 11), or, in a 'dark' (i.e. unirradiated—lane 10) control. To test whether the cleavages observed arose uniquely from oxidation by the attached anthraquinone functionality, and also to test whether such putatively AQ-dependent cleavages occurred strictly in intra-molecular fashion, photo-irradiation was carried out on samples containing mixtures of $^{32}$P-end-labeled constructs lacking anthraquinone and unlabeled constructs conjugated to anthraquinone. Lanes 7 and 14 show that no significant cleavage in the labeled strands was observed, either for the double-stranded control or the integrated-ligand sensor construct.

Figure 13A:
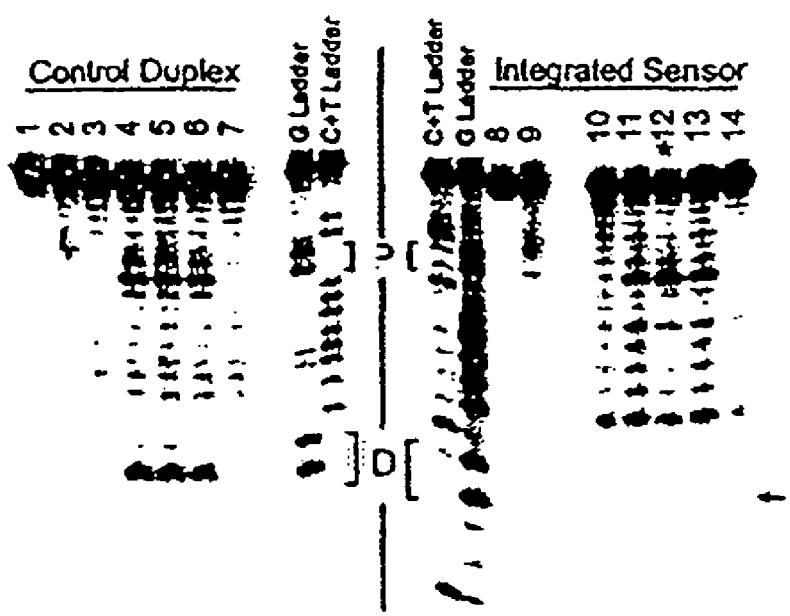
FIG. 13(a) comprise phosphorimager traces of strand-cleavage data from the "integrated-ligand" sensor (lanes 8-14), and, from its duplex control (lanes 1-7). "P" and "D" indicate the positions of the proximal and distal guanine doublets shown in FIG. 12. Lanes 4 and 11 show the control duplex and integrated sensor constructs photo-irradiated in the 'Mg—Na' buffer (50 mM Tris-Cl, pH 7.9, 2.5 mM $MgCl_2$, 100 mM NaCl and 0.1 mM EDTA) with no added adenosine. Lanes 5 and 12 included 2.5 mM adenosine, and lanes 6 and 13 included 2.5 mM uridine. Lanes 3 and 10 show background piperidine cleavage (using the same conditions as with the other samples) for non-photo-irradiated ("dark") controls for the duplex construct and for the AQ-labeled sensor construct, respectively. Lanes 1 and 8 show constructs that were neither irradiated nor piperidine-created, while lanes 2 and 9 show constructs that were photo-irradiated but not piperidine treated. Lanes 7 and 14 show controls where $^{32}$P-end labeled constructs lacking AQ were photo-irradiated in the presence of unlabeled constructs possessing the AQ-functionality. Maxam-Gilbert sequencing reactions were used to generate the "G" and "C+T" ladders. All photo-irradiation was with a 366 nm low-pressure lamp for 90 minutes (45 minutes for double-stranded controls) at 18° C., from a distance of 4 cm. Samples were then piperidine treated and run on a 12% sequencing gel (11% for double stranded control).

The fact that in the integrated-ligand sensor high levels of strand cleavage were observed only at the proximal ("P") guanine doublet in the presence of uridine (lane 13), as well as in the absence of added nucleosides (lane 11, FIG. 13(a)), indicated that charge transport in these cases was localized almost exclusively within the AQ stem 16 (as depicted in the model for this sensor 10 in FIG. 11). By contrast, when 2.5 mM adenosine was present (lane 12) the same experimental procedure resulted in 5.0% cleavage at the distal ("D") guanine doublet (up from 0.26% shown in lanes 11 and 13) when photo-irradiated for 90 minutes. This reflects a ~20 fold enhancement in strand-cleavage enhancement in the presence of the adenosine ligand analyte 12. This observation indicates that the adenosine-induced folded structure of the aptamer receptor 20 was indeed capable of facilitating charge transfer between the first (detector) and second (AQ) stems 14, 16. Interestingly, in the presence of adenosine, even the "P" doublet showed a small enhancement in cleavage (<2 fold), consistent with an overall tightening and stabilization of the sensor construct.

Figure 13B:
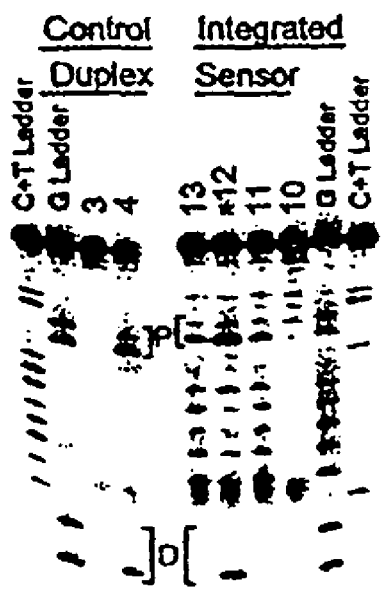
FIG. 13(b) are phosphorimager traces as in FIG. 13(a) but carried out in Mg buffer (50 mM Tris-Cl, pH 7.9, 2.5 mM MgCl2, and 0.1 mM EDTA) with photo-irradiation of 120 minutes at 18° C.

When experiments similar to the above were carried out in the absence of NaCl (i.e. in the 'Mg' buffer: 50 mM Tris-Cl, pH 7.9, 2.5 mM MgCl$_2$, and 0.1 mM EDTA), somewhat different results were observed (FIG. 13B). The double-stranded control showed comparable cleavage patterns as seen in the 'Mg—Na' buffer, i.e. strand cleavage was observed at the proximal (P) and distal (D) guanine doublets both in the absence (lane 4) or presence (data not shown) of 2 mM adenosine (relative to the 'dark' control—lane 3). By contrast, the integrated sensor construct exhibited significant strand cleavage: at the distal (D) guanine doublet in the presence of 2 mM added adenosine (lane 12)—as also seen in the 'Mg—Na' buffer (FIG. 13(a). This increase in strand cleavage, from 0.98% to 7.3%, describes a ~7 fold enhancement in the presence of adenosine.

The major difference observed for the sensor construct in the 'Mg' buffer (FIG. 13(b)), relative to the 'Mg—Na' buffer (FIG. 13A), was that in the 'Mg' buffer enhanced cleavage occurred at the proximal (P) guanine doublet in the presence of adenosine (lane 12 versus lanes 11 and 13, FIG. 13(b)). This enhanced cleavage may reflect a proportionately greater stabilization of the duplex elements flanking the aptamer receptor 20 by the aptamer-bound adenosines in this relatively low-salt buffer. The inventors believe that this enhanced proximal G cleavage was not a consequence of the re-association of the strands of the sensor construct dissociated in the 'Mg' buffer (non-denaturing gel electrophoresis experiments showed that the constructs remained intact in all buffers and experimental conditions used in this study—data not shown).

Figure 14:
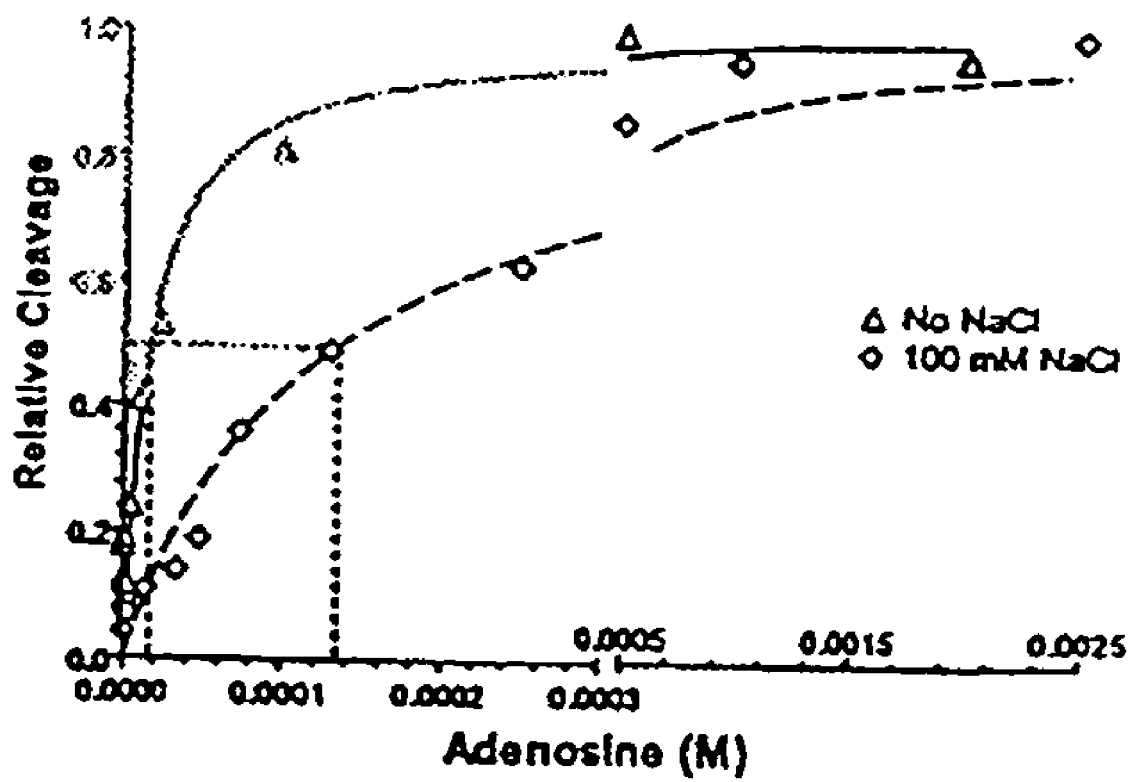
FIG. 14 is a graph showing adenosine-dependence of cleavage at the distal guanines of the "integrated-ligand" sensor construct. Samples of the sensor construct (0.5 μM) were photo-irradiated for 90 minutes at 18° C. in Mg buffer containing or not containing Na, in the presence of various adenosine concentrations. Following irradiation, samples were piperidine treated and loaded on sequencing gels. Strand cleavage, quantitated in a phosphorimager, were corrected against 'dark,' non-irradiated, controls and normalized for the maximal observed cleavage.

Variations in solution conditions also affected the efficiency of strand cleavage at the distal (D) guanine doublet as a function of adenosine concentration. FIG. 14 shows how in different solutions different binding affinities were observed for the adenosine ligand. In the 'Mg' buffer, half maximal strand cleavage was observed at 18 μM adenosine, while in the 'Mg—Na' buffer, it was observed at 135 μM adenosine.

2.3.2 The Coupled-Ligand Sensor.

Figure 15A:
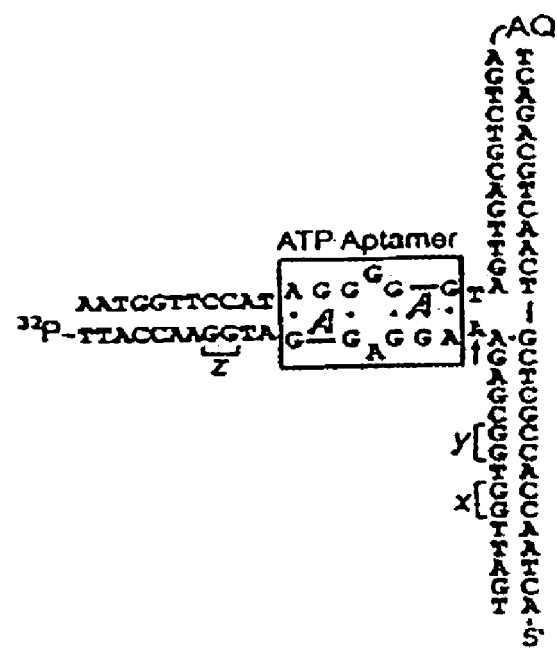
FIG. 15(a) shows the structure and sequence of the "coupled-ligand" sensor (SEQ ID NO: 5, SEQ ID NO: 6, and SEQ ID NO: 7). The ATP aptamer domain is indicated as boxed, while the two bound adenosines are indicated by outlined 'A's. Guanine doublets in the 5'-32P-end labeled strand used to monitor charge transfer to the Sensor and Detector stems are indicated as "x", "y", and "z". The AoG mismatch at the junction was used since it gave superior results relative to Watson-Crick base pairs at that position. The arrow, on an adenine at the junction, indicates an adenine that showed an unusually high cleavage (see FIG. 15(b), lane 4, below).
Figure 15B:
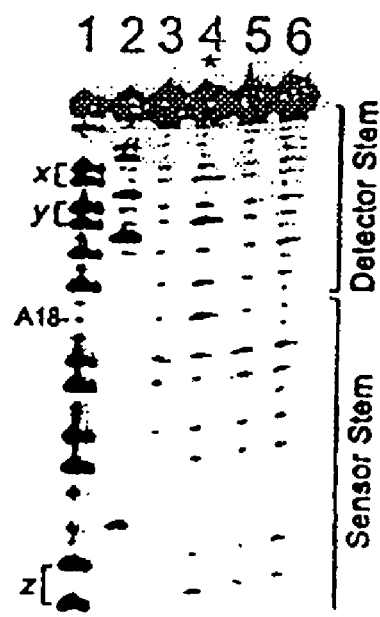
FIG. 15(b) are Phosphorimager traces of strand-cleavage data from the "coupled-ligand" sensor construct, irradiated at 18° C. for 180 minutes in the 'Mg—Na' buffer. Lanes 3-5 show cleavage results in the presence of 2.5 mM uridine (lane 3); 2.5 mM adenosine (lane 4); and, buffer alone (lane 5). Lanes 1 and 2 show the Maxam-Gilbert "G" and "C+T" ladders, respectively. Lane 6 shows the background piperidine cleavage of the non-irradiated construct.

The properties of a different sensor design, the "coupled-ligand" sensor (which also utilized the ATP aptamer, and is shown schematically in FIG. 11, lower) were also examined. This second design does not depend on the conductive property of the folded aptamer domain. The predicted lack of base stacking between the third stem (i.e. sensor) 22 stem and either of the first and second stems 14, 16 in the folded state was expected to prevent electron transfer between these regions. A coupled-ligand sensor 10 of this design, for detecting adenosine, was assembled from the DNA oligomers shown in FIG. 15(a). In this construct, the aptamer bulge was separated from the three-way junction 18 by a single A-T base pair. To detect charge transfer in the various sterns, the DNA strand shared by both the first and third stems 14, 22 was 5'-$^{32}$P-labelled. FIG. 15(b) shows the results obtained when samples were irradiated in the 'Mg—Na' buffer for 180 minutes. In the absence of added adenosine (lane 5), or in the presence of 2.5 mM uridine, no detetctable cleavage above the background level (lane 6) was observed at all positions. In the presence of 2.5 mM adenosine (lane 4), however, significantly enhanced strand cleavage (>15 fold enhancement in replicate experiments) was seen at the 5' guanine of each of the two-guanine doublets present in the first stem 14 (indicated as x and y). Lack of detectable cleavage at these guanines in the absence of adenosine prevented the determination of an absolute ratio for cleavage enhancement; however, the lower limit indicated above (>15 fold) could be calculated. A comparable enhancement, however, was not observed for the doublet (z) located in the third stem 22 (2-4 fold increase) as predicted by a structural model of this DNA construct. Irradiation experiments on a control construct for the above three-way junction 18, that lacked the aptamer bulge but incorporated a Watson-Crick duplex (as with the 'integrated sensor'—see above) in place of the aptamer 'arm', yielded no modulation of strand cleavage in the presence of added adenosine (data not shown).

The effect of different buffer conditions on strand cleavage in this construct was not examined, as non-denaturing electrophoresis experiments indicated that this sensor construct was not sufficiently stable structurally in the low-salt 'Mg' buffer (data not shown).

3.0 Discussion

Experiments with the above two sensor designs, utilizing the ATP aptamer as a receptor 20, clearly demonstrate the utility of DNA conformational changes (resulting from the adaptive binding of analyte 12 to the DNA aptamer) in modulating charge-transfer through DNA.

Investigations with the integrated-ligand sensor 10; above, have demonstrated that both the sensitivity of and signal enhancement from analyte-sensing depend significantly on solution conditions. It remains unclear whether such differences reflect purely structural transformations of the aptamer in the different ionic strength solutions or whether they also reflect changes in the process of charge-transfer through DNA.

Comparison of the behavior of the integrated sensor 10 in the two ionic strength conditions tested indicates a trade-off between signal enhancement and sensitivity. In the relatively low-salt 'Mg' buffer a half maximal enhancement of ~3.5 fold enhanced cleavage at the distal ("D") guanine doublet was observed with 18 µM adenosine, whereas in the higher salt 'Mg—Na' buffer a half maximal enhancement of ~10 fold was observed with 130 µM adenosine. In other words, the addition of 100 mM NaCl generated a highly amplified signal, but at the cost of a lower sensitivity of adenosine detection. Such an unusual trend may result from the aptamer forming a subtly altered structure under higher ionic strength conditions, one that requires higher adenosine concentrations to drive the equilibrium to the adenosine-bound form. The guanine rich aptamer domain could potentially form foldback G-G base pairs or guanine quartets in the presence of NaCl[38-39]. In fact, guanine quartets were originally postulated to be a part of the folded aptamer structure when the aptamer was originally identified[28].

In addition, care must be taken in interpreting the results of the adenosine dependence data from FIG. 14, since the curves may not directly reflect the binding affinities of the aptamer for its ligand. As described above, each molecule of this particular aptamer binds two molecules of the adenosine ligand, and it is unclear whether the binding of only one molecule of ligand allows charge transfer to occur to some extent or not.

Comparing the efficiencies of conduction through particular DNA sequences has often been accomplished by comparing the ratios of cleavage at "proximal" and "distal" guanines (D/P or P/D ratios)[7,8,34,26,40,41]. This comparison is an indicator of the efficiency with which charge transfer proceeds through a specified sequence of interest that is flanked by isolated guanines, doublets, triplets, or reactive bases such as 8-oxoguanine[9] or 7-deazaguanine[41]. A comparison of conduction through the integrated sensor and through its double-stranded control gave D/P ratios, respectively, of 0.48±0.07 versus 0.23±0.04 in the 'Mg—Na' buffer; and, 0.4±0.08 versus 0.24±0.05 in the 'Mg' buffer. Comparing these ratios at face value suggests that the aptamer domain is a somewhat superior conductor compared to the double-stranded DNA control. However, direct comparisons of the sensor 10 and the duplex control may not be entirely appropriate. When irradiation experiments were carried out such that comparable levels of strand cleavage were achieved at the distal ("D") guanine doublets in both the control and sensor constructs, a two-fold higher cleavage was observed at the proximal ("P") guanine doublet of the double stranded control. The reduced efficiency of cleavage at the proximal guanines in the sensor construct must reflect a hindrance to charge migration into sequences influenced by the presence of the aptamer, given that the double stranded proximal stems are identical in both the sensor and double stranded constructs. Once a mobile charge reaches the proximal ("P") guanine doublet, it then appears that the 'integrated-ligand' sensor better facilitates the transfer of that charge to the distal ("D") guanine doublet in comparison to the double stranded control. A possible reason for the lower D/P ratios seen in the duplex control may result from the GG doublets situated between the "P" and "D" doublets on the AQ-modified strand (FIG. 12). These intervening doublets may be acting as 'traps', thus reducing the efficiency of charge transfer to the distal ("D") guanine doublet of the duplex control. Overall, it is still remarkable that the folded, non-B-DNA aptamer possesses a comparable if not more favorable conductive property than the B-DNA duplex control.

Besides the capacity of the ATP aptamer to modulate charge transfer between the acceptor and detector stems, interesting observations were made regarding the aptamer domain, specifically. Cleavage at the guanines located within the aptamer domain was observed to be low in both of the buffers used (FIG. 13(a) & 3(b), lanes 11-13). Low cleavage in the absence of bound adenosine was lowered further upon the binding of adenosine. This observation may reflect the non-B helical structure of the folded aptamer domain. The high level of oxidation of the 5'-most guanine in guanine doublets is strictly true only for double-stranded B-DNA[42]. Single-stranded sequences[10], and guanine quadruplexes[43], for instance, do not show this pattern. This property of the aptamer guanines may explain the lower D/P ratio of the sensor, relative to that of the duplex control.

The demonstrated capacity of the DNA aptamer for adenosine/ATP to act as a conduit for charge transfer in the folded state is a property not likely shared by all aptamer motifs. In addition to inherent conductivity differences between different aptamers, some aptamers, which are not formed from internal (bulge) loops, may not easily be incorporated into duplex DNA. To design a more general sensor, capable of utilizing diverse receptors and aptamers, and responding to a variety of ligands/analytes, an immobile three-way helical junction was used as a starting point for a second design. This 'coupled-ligand' sensor (FIG. 15(a)) also exhibited modulation of charge transfer from the Acceptor to Detector stems in response to adenosines binding to the aptamer element. This construct, however, required longer irradiation times (relative to that required for the integrated sensor) to obtain significant levels of cleavage at the guanine doublets (x and y in FIG. 15(a)) in the Detector stem. It remains to be investigated whether the lower charge transfer efficiency in the 'coupled-ligand' construct arose from the particular sequences chosen for the stems, or from the presence of the 3-way junction. Future work will also focus on determining the three-dimensional structure of this 3-way junction, in order to understand why significantly more strand cleavage was observed in the Detector stem compared to the Sensor stem.

A deeper characterization of the 'coupled-ligand' sensor design, and of related architectures, is desirable given their broad potential for development as modular sensors. In the 'coupled-ligand' sensor there is only a requirement for a conformational change in the analyte-binding (aptamer or receptor) domain upon the binding of the analyte, and not for an inherent ability of the binding domain to permit charge transfer through its own structure. The side-on placement of the analyte receptor should also be applicable in the design of hybrid sensors that are not composed entirely of DNA. Such hybrid systems may possess binding domains consisting of RNA, proteins or other organic "host" entities (such as crown ethers, cryptands, and others) that undergo a conformational change upon binding the appropriate "guest" molecule or ion.

The guanine damage- and electrophoresis-based detection methodology used in this Example were necessary for single-nucleotide resolution investigations of the charge conduction pathways in the sensors. Here, we have used them to demonstrate that ligand-induced conformational changes can indeed be used to modulate charge transfer through DNA. However, to develop this technology for the rapid detection of ligand molecules other detection methodologies will need be employed. The most likely scenario would have the DNA sensor constructs functionalized onto metal or other surfaces such that direct measurements of current flow can be made. Reports of successful coupling of modified DNA to electrodes and the direct monitoring (by chemical reaction in solution or photo-excitation) of hybridization via charge transfer through the resulting duplex[5,44-45], suggests that aptamers can also be used in this way towards the development of novel DNA-based sensors.

For the applicability of this technology as a practical detection method, the sensitivity of detection must be sufficient. As described, the sensitivity of this system is limited by the affinity of the incorporated a aptamer sequence for its target ligand (given that the magnitude of the signal is proportional to the fraction of sensor constructs bound with ligand). The ATP aptamer described in this Example possesses a dissociation constant in the μM range for the adenosine ligand. Such a binding affinity would be insufficient for a practical sensor intended to monitor, for instance, hormone levels in blood (for which, sensor-analyte affinities in the low nM to high pM range would be required). Binding affinities of the nM-pM range, however, are possible and have been obtained with nucleic acid aptamers; for example, an RNA aptamer selected for binding to the aminoglycoside antibiotic tobramycin, possessed a binding constant of 770 pM[46].

More broadly, the receptor component of such DNA sensors need not in itself be composed of DNA or RNA as discussed above. Organic or inorganic hosts, which undergo significant conformational change upon binding their cognate guest could, in principle, be incorporated in place of DNA or RNA aptamers into the design of such sensors.

Harnessing the potential of conformational switches in nucleic acids is a relatively new endeavor. It has been used, to date, in the development of a mechanical switch[47], allosteric enzymes[48] and, now, electronic devices. The ability to monitor the presence and concentration of analytes electrically promises the development of rapid, DNA-based, solid-state" detection devices for virtually any compound.

As will be apparent to those skilled in the art in the light of the foregoing disclosure, many alterations and modifications are possible in the practice of this invention without departing from the scope thereof. Accordingly, the scope of the invention is to be construed in accordance with the substance defined by the following claims.

What is claimed is:

1. An analyte sensor comprising:
   (a) a first oligonucleotide stem comprising a plurality of base pairs capable of permitting charge conduction along a length of said first stem;
   (b) a second oligonucleotide stem comprising a plurality of base pairs capable of permitting charge conduction along a length of said second stem;
   (c) a receptor site capable of binding said analyte, wherein said receptor site is an aptamer operatively connected to said first oligonucleotide stem and said second oligonucleotide stem; and
   (d) a charge flow inducer coupled to one of said first and second stems for triggering charge flow in at least one of said first and second stems,
   wherein said sensor is alterable between a first conformational state substantially impeding charge transfer between said first and second stems and a second conformational state permitting charge transfer between said first and second stems, wherein said sensor switches between said first conformational state and said second conformational state when said analyte binds to said receptor site.

2. The sensor as defined in claim 1, wherein said charge is transferred between said first and second stems through said receptor site in said second conformational state.

3. The sensor as defined in claim 1, wherein said receptor site is removed from a conduction path between said first and second stems in said second conformational state.

4. The sensor as defined in claim 1, wherein said sensor switches from said first conformational state to said second conformational state when said analyte binds to said receptor site.

5. The sensor as defined in claim 1, wherein said receptor site is selected from the group consisting of nucleic acids and proteins.

6. The sensor as defined in claim 5, wherein said receptor site comprises a nucleic acid aptamer selected for binding affinity to a target analyte.

7. The sensor as defined in claim 1, wherein said receptor site is capable of binding to analytes which do not ordinarily bind to DNA.

8. The sensor as defined in claim 1, wherein said first and second stems each comprise an ordered sequence of nucleotide base pairs, and wherein said sensor comprises a switch region at the junction between said first and second stems, wherein spacial stacking of said first and second stems is said switch region substantially impedes charge transfer between said first and second stems in said first conformational state.

9. The sensor as defined in claim 8, wherein said switch region comprises unpaired nucleotides in said first conformational state.

10. The sensor as defined in claim 9, wherein said unpaired nucleotides are non-Watson-Crick nucleotides.

11. The sensor as defined in claim 9, wherein the spacial stacking of said first and second stems within said switch region is altered when said sensor switches between said first and second conformational states.

12. The sensor as defined in claim 11, wherein said switch region is located proximate to said receptor site.

13. The sensor as defined in claim 8, wherein said first and second stems each comprise a multi-stranded DNA helix.

14. The sensor as defined in claim 13, wherein said helix is disrupted in said switch domain in the vicinity of said receptor site in said first conformational state.

15. The sensor as defined in claim 1, further comprising a third oligonucleotide stem comprising said receptor site.

16. The sensor as defined in claim 15, wherein said first, second and third stems are connected together at a three-way junction.

17. The sensor as defined in claim 16, wherein at least one of said first, second and third stems comprises a non-Watson-Crick base pairing in the vicinity of said three-way junction.

18. The sensor as defined in claim 15, further comprising a fourth oligonucleotide stem, wherein said first, second, third and fourth stems are connected together at a four-way junction.

19. The sensor as defined in claim 1, wherein said charge flow inducer comprises an excitable moiety alterable between an unexcited and an excited state.

20. The sensor as defined in claim 19, wherein said moiety is an oxidizing agent in said excited state.

21. The sensor as defined in claim 19, wherein said moiety is selected from the group consisting of anthraquinone and rhodium (III).

22. The sensor as defined in claim 1, further comprising a detector electrically coupled to said first stem for directly measuring said charge transfer.

23. The sensor as defined in claim 22, wherein said detector comprises a conductor.

24. The sensor as defined in claim 1, wherein said receptor site binds adenosine analyte.

25. A nanoelectronic chip comprising a plurality of sensors as defined in claim 1.

26. A sensor for detecting first and second analytes comprising:
(a) a first oligonucleotide stem comprising a plurality of base pairs capable of permitting charge conduction along a length of said first stem;
(b) a second oligonucleotide stem comprising a plurality of base pairs capable of permitting charge conduction along a length of said second stem;
(c) a first receptor site comprising a first aptamer capable of binding said first analyte; and
(d) a second receptor site comprising a second aptamer capable of binding said second analyte,
wherein said first and second receptor sites are operatively connected to said first and second oligonucleotide stems, wherein said sensor is alterable between a first conformational state substantially impeding charge transfer between said first second stems and a second conformational state permitting charge transfer between said first and second stems; and
(e) a charge flow inducer coupled to one of said first and second stems for triggering charge flow in at least one of said first and second stems, wherein said sensor switches between said first conformational state and said second conformational state when said first analyte binds to said first receptor site and said second analyte concurrently binds to said second receptor site.

27. A method for detecting the presence of an analyte comprising:
(a) providing a sensor as defined in claim 1 having a receptor capable of binding to said analyte;
(b) inducing a charge flow in one of said first and second stems of said sensor; and
(b) detecting any change in charge transfer between said first and second stems upon binding of said analyte to said receptor.

28. The method as defined in claim 27, wherein the step of detecting any change in charge transfer comprises electrically coupling a detector to the other of said first and second stems of said sensor.

29. The method as defined in claim 27, wherein the step of inducing a net charge comprises:
(a) coupling a moiety to said second stem alterable between an unexcited and an excited state; and
(b) exciting said moiety to form an oxidizing agent.

30. The method as defined in claim 29, wherein the step of detecting any change in charge transfer comprises testing for the formation of oxidation products of said sensor.

31. The method as defined in claim 30, wherein said testing comprises:
(a) heating said sensor in the presence of piperidine; and
(b) separating any reaction products of step (a) by gel electrophoresis.

32. An analyte sensor comprising:
(a) a first oligonucleotide stem comprising a plurality of base pairs capable of permitting charge conduction along a length of said first stem;
(b) a second oligonucleotide stem comprising a plurality of base pairs capable of permitting charge conduction along a length of said second stem;
(c) an aptamer site capable of binding said analyte, wherein said aptamer site is operatively connected to said first oligonucleotide stem and said second oligonucleotide stem, and
(d) a charge flow inducer coupled to one of said first and second stems for triggering charge flow in at least one of said first and second stems,
wherein said sensor is alterable between a first conformational state substantially impeding charge transfer between said first and second stems and a second conformational state permitting charge transfer between said first and second stems, wherein said sensor switches between said first conformational state and said second conformational state when said analyte binds to said aptamer site, and wherein the aptamer site is capable of binding to analytes which do not ordinarily bind to DNA.

33. A sensor for detecting first and second analytes comprising:
(a) a first oligonucleotide stem comprising a plurality of base pairs capable of permitting charge conduction along a length of said first stem;
(b) a second oligonucleotide stem comprising a plurality of base pairs capable of permitting charge conduction along a length of said second stem;
(c) a first aptamer site capable of binding said first analyte;
(d) a second aptamer site capable of binding said second analyte; and
(e) a charge flow inducer coupled to one of said first and second stems for triggering charge flow in at least one of said first and second stems,
wherein said first and second aptamer sites are operatively connected to said first and second oligonucleotide stems, wherein said sensor is alterable between a first conformational state substantially impeding charge transfer between said first and second stems and a second conformational state permitting charge transfer between said first and second stems, wherein said sensor switches between said first conformational state and said second conformational state when said first analyte binds to said first aptamer site, and said second analyte concurrently binds to said second aptamer site, and wherein at least one of the aptamer sites is capable of binding to analytes which do not ordinarily bind to DNA.

34. A method for detecting the presence of an analyte comprising:
(a) providing a sensor as defined in claim 1 comprising said aptamer capable of binding to said analyte;
(b) inducing a charge flow in one of said first and second stems of said sensor; and
(c) detecting any change in charge transfer between said first and second stems upon binding of said analyte to said aptamer.

35. An analyte sensor comprising:
(a) a first oligonucleotide stem comprising a plurality of base pairs capable of permitting charge conduction along a length of said first stem;
(b) a second oligonucleotide stem comprising a plurality of base pairs capable of permitting charge conduction along a length of said second stem;
(c) a receptor site capable of binding said analyte, wherein said receptor site is an aptamer operatively connected to said first oligonucleotide stem and said second oligonucleotide stem for modulating charge transfer therebetween; and
(d) a charge flow inducer coupled to one of said first and second stems for triggering charge flow in at least one of said first and second stems,
wherein said sensor is alterable between a first conformational state substantially impeding charge transfer between said first and second stems and a second conformational state permitting charge transfer between said first and second stems, wherein said sensor switches from said first conformational state to said second conformational state when said analyte binds to said receptor site.

36. An analyte sensor comprising:
(a) a first oligonucleotide stem comprising a plurality of base pairs capable of permitting charge conduction along a length of said first stem;
(b) a second oligonucleotide stem comprising a plurality of base pairs capable of permitting charge conduction along a length of said second stem;
(c) a receptor site capable of binding said analyte, wherein said receptor site is an aptamer operatively connected to said first oligonucleotide stem and said second oligonucleotide stem for modulating charge transfer therebetween; and
(d) a charge flow inducer coupled to one of said first and second stems for triggering charge flow in at least one of said first and second stems,
wherein said sensor is alterable between a first conformational state substantially impeding charge transfer between said first and second stems and a second conformational state permitting charge transfer between said first and second stems, wherein said sensor switches from said second conformational state to said first conformational state when said analyte binds to said receptor site.

37. The sensor as defined in claim 1, wherein said sensor comprises a switch region at the junction between said first and second stems, wherein spacial stacking of nucleotides in said switch region is disrupted in said first conformational state which substantially impedes charge transfer between said first and second stems.

38. The sensor as defined in claim 37, wherein binding of said analtye to said aptamer causes a conformational change which permits spacial stacking of nucletotides in said switch region in said second conformational state resulting in establishment of charge transfer between said first and second stems.

39. The sensor as defined in claim 37, wherein said nucleotides in said switch region comprise unpaired nucleotide bases in said first conformational state.

40. The sensor as defined in claim 1, wherein said sensor comprises a switch region at the junction between said first and second stems, wherein nucleotides in said switch region are orderly stacked in said first conformational state which permits charge transfer between said first and second stems.

41. The sensor as defined in claim 40, wherein binding of said analtye to said aptamer causes a conformational change which disrupts spacial stacking of nucleotides in said switch region in said second conformational state thereby impeding charge transfer between said first and second stems.

42. The sensor as defined in claim 41, wherein said nucleotides in said switch region comprise unpaired nucleotide bases in said second conformational state.

* * * * *

SEQUENCE LISTING

<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
atcaaggttc ctcctggcta aa                                          22

<210> SEQ ID NO 2
<211> LENGTH: 22
<212> TYPE: DNA
<213> ORGANISM: Artificial Sequence
<220> FEATURE:
<223> OTHER INFORMATION: Synthetic Construct

<400> SEQUENCE: 2
tttagccagg aggaaccttg at                                          22

<210> SEQ ID NO 3
<211> LENGTH: 22
<212> TYPE: DNA

```
<213> ORGANISM: Artificial Sequence
<220> FEATURE:
<223> OTHER INFORMATION: Synthetic Construct

<400> SEQUENCE: 3
atcaaggtgg gggatggcta aa                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
tttagccagg aggaaccttg at                                              22

<210> SEQ ID NO 5
<211> LENGTH: 31
<212> TYPE: DNA
<213> ORGANISM: Artificial Sequence
<220> FEATURE:
<223> OTHER INFORMATION: Synthetic Construct

<400> SEQUENCE: 5
agtctgcagt tgatggggga taccttggta a                                    31

<210> SEQ ID NO 6
<211> LENGTH: 33
<212> TYPE: DNA
<213> ORGANISM: Artificial Sequence
<220> FEATURE:
<223> OTHER INFORMATION: Synthetic Construct

<400> SEQUENCE: 6
ttaccaaggt aggaggaaag agcggtggtt agt                                  33

<210> SEQ ID NO 7
<211> LENGTH: 28
<212> TYPE: DNA
<213> ORGANISM: Artificial Sequence
<220> FEATURE:
<223> OTHER INFORMATION: Synthetic Construct

<400> SEQUENCE: 7
actaaccacc gctcgtcaac tgcagact                                        28
```